United States Patent [19]

Chen et al.

[11] Patent Number: 5,864,022

[45] Date of Patent: *Jan. 26, 1999

[54] PROCESS FOR THE MANUFACTURE OF 3-AMINO-SUBSTITUTED GLYCOSYLATED BILE ACIDS

[75] Inventors: Anna K. Chen, Rahway; Ramesh Kakarla; Dashan Liu, both of East Brunswick; Michael J. Sofia, Lawrenceville; Thomas C. Zebovitz, Colonia, all of N.J.

[73] Assignee: Intercardia, Inc., Research Triangle, N.C.

[*] Notice: The term of this patent shall not extend beyond the expiration date of Pat. No. 5,585,470.

[21] Appl. No.: 822,849

[22] Filed: Mar. 24, 1997

Related U.S. Application Data

[62] Division of Ser. No. 494,194, Jun. 23, 1995, Pat. No. 5,693,770, which is a continuation of Ser. No. 264,310, Jun. 23, 1994, Pat. No. 5,585,470.

[51] Int. Cl.[6] .............. C07J 3/00; C07G 3/00; C07G 17/00
[52] U.S. Cl. .............. 536/5; 536/18.5; 536/124
[58] Field of Search .............. 536/5, 18.5, 124, 536/106

[56] References Cited

U.S. PATENT DOCUMENTS 5,338,837   8/1994   Kahne ........................... 536/5
5,514,658   5/1996   Benito et al. ................... 514/25

FOREIGN PATENT DOCUMENTS

WO93/11772   6/1994   WIPO .

OTHER PUBLICATIONS

Kahne, D. et al., *J. Am. Chem. Soc.*, (1989),111:6881–6882.
Blickenstaff, R., et al.,*J. of Chem*, (1973), 38(7):1276–1279.
Blickenstaff, R., et al.,*J. of Chem*, (1971), 36(9):1271–1276.
Werner and Wess, *Tet. Lett.*, (1992) 33(2):195–198.
Fiegel, Martin, *Tet. Lett.*, (1994) 35(4):565–568 (and German language version, *Chem. Abstract*, 115:P72019d).
*J. Carb. Chem.*, (1994) 13(2):141–161.
Per–Mikael Åberg, et al. –Large Scale Synthesis of Two Trisaccharide Spacer Glycosides Corresponding to the Blood Group A and B Determinants Using Thioglysosides and Dimethyl (Thiomethyl) Sulfonium Tetrafluoroborate (DMTSB) as Promoter—*J. Carb. Chem. 13(2)*, p. 141–161, (1994).
Wolf et al. "Intramolecular Catalysis. VI. Selectivity in 7alpha, 12alpha–Dihydroxy Steroids and Enhancement of 12 alpha–Hydroxyl Reactivity by Substituents at Carbon 3, " J. Org. Chem. (1973) 38(3): 1276–1279.

*Primary Examiner*—Jon P. Weber
*Assistant Examiner*—Susan Hanley
*Attorney, Agent, or Firm*—Gilberto M. Villacorta, Pepper Hamilton LLP

[57] ABSTRACT

The present invention relates to a process for the preparation and manufacture of 3-amino-substituted glycosylated bile acid derivatives. Intermediates and related compounds are also disclosed. In particular, the present invention permits the conversion of cholic acid esters to the 3-amino-7,12-bis (glucosyl)cholic acid esters via an azide intermediate. Conditions for the purification and isolation of the desired product is also disclosed to provide an overall manufacturing process suitable for large-scale production.

26 Claims, 9 Drawing Sheets

Methyl cholate
methanol

Azide
methanol

Phenylthio tetrabenzylglucoside
triturated with hexane
ethyl acetate

Sulfoxide
methylene chloride/ hexane
ethyl acetate/hexane

Glycosylated azide
ethanol
methylene chloride/hexane
ethyl acetate/hexane
isopropanol

PROCESS FOR THE MANUFACTURE OF 3-AMINO-SUBSTITUTED GLYCOSYLATED BILE ACIDS

This specification is a divisional of application of Ser. No. 08/494,194 filed Jun. 23, 1995 now U.S. Pat. No. 5,693,770 which is a continuation of application Ser. No. 08/264,310 filed Jun. 23, 1994 now U.S. Pat. No. 5,585,470 incorporated herein by reference.

TECHNICAL FIELD

The present invention relates to a process for the synthesis and manufacture of 3-amino-substituted glycosylated bile acid derivatives, including a new process for the manufacture of a protected sugar moiety useful in the glycosylation step.

BACKGROUND ART

The 3-amino-substituted glycosylated bile acid derivatives are disclosed in International Publication No. WO 93/11772. These and their related compounds are described as permeation enhancers; that is, these compounds enhance the ability of therapeutically significant compounds to penetrate biological or synthetic membranes. This property of permeation enhancement is observed whether the therapeutically significant compound is combined with the permeation enhancer as an admixture or as a conjugate therewith.

Hence, from a commercial point of view, an efficient synthetic scheme for the preparation of such permeation enhancers, particularly the 3-amino-substituted glycosylated bile acid derivatives, would be extremely attractive.

It should further be pointed out that the commercial attractiveness of a large-scale manufacturing process of 3-amino-substituted glycosylated bile acids (and many of their derivatives) would be enhanced by an abundant supply of phenyl 2,3,4,6-tetrabenzylthioglucose, the preferred initial protected form of the sugar moiety used in the glycosylation of the bile acids and their derivatives.

Earlier efforts were directed toward the one-step conversion of commercially available 2,3,4,6-tetra-O-benzyl-D-glucopyranose to the phenyl 2,3,4,6-tetrabenzylthioglucose compound via treatment with tri-n-butylphosphine/diphenyldisulfide (in 46% yield). These starting materials and/or reagents are quite costly. The tetrabenzylglucopyranose alone is priced at ca. $7,000/kg.

Accordingly, a more economical method of preparing the desired phenyl tetrabenzylthioglucose would, likewise, be a welcome advance.

DISCLOSURE OF THE INVENTION

The present invention is directed to a process for the synthesis and manufacture of 3-amino-substituted glycosylated bile acids. Generally, the synthesis can be achieved from a widely available starting material, such as cholic acid. After esterification of the cholic acid side chain, the 3-hydroxy group is converted to a suitable leaving group, such as a tosylate or a mesylate.

Nucleophilic displacement of the leaving group, with inversion of stereochemistry, is performed using an azide reagent. Subsequently, the resulting 3-azido derivative is subjected to a sulfoxide-based bisglycosylation procedure to provide the 3-azido-substituted bisglycosylated cholic acid ester. Alternatively, the 3-tosyloxy or 3-mesyloxy cholate ester is first converted to a bisglycosylated intermediate, which is subsequently transformed to the 3-azido bisglycosylated bile acid product.

Reduction of the azido group to the corresponding amine, followed by removal of any protecting groups present on the sugar moieties, provides the desired 3-amino-substituted glycosylated bile acid.

In addition, a novel procedure for the preparation of a preferred initial protected sugar moiety, used in the glycosylation step, is also described. The novel procedure is applicable for the synthesis of a wide range of protected sugar moieties and is exemplified by the synthesis of a phenyl tetrabenzylthioglucose. In the present invention, a three-step process is described, starting with inexpensive glucose pentaacetate ($48/kg).

The final overall yield of the tetrabenzylthioglucose (53%) is comparable to the one-step process described previously (46%). While two additional steps are required in the invention, the cost of reagents is drastically reduced. In addition, the overall chemistry is simplified and made more amenable to scale-up synthesis.

What is more, a one-step combination procedure for reduction of the azide group to an amine and deprotection of the sugar moieties is disclosed.

Conditions for the purification and isolation of the desired product is also disclosed to provide an overall manufacturing process suitable for large-scale production.

Other objects of the present invention include the disclosure of isolation and purification methods, including a description of the solvent mixtures suitable for recrystallization of reagents, intermediates, or products, as well as purification of selected compounds by reverse-phase column chromatography.

BEST MODE FOR CARRYING OUT THE INVENTION

Figure 1:
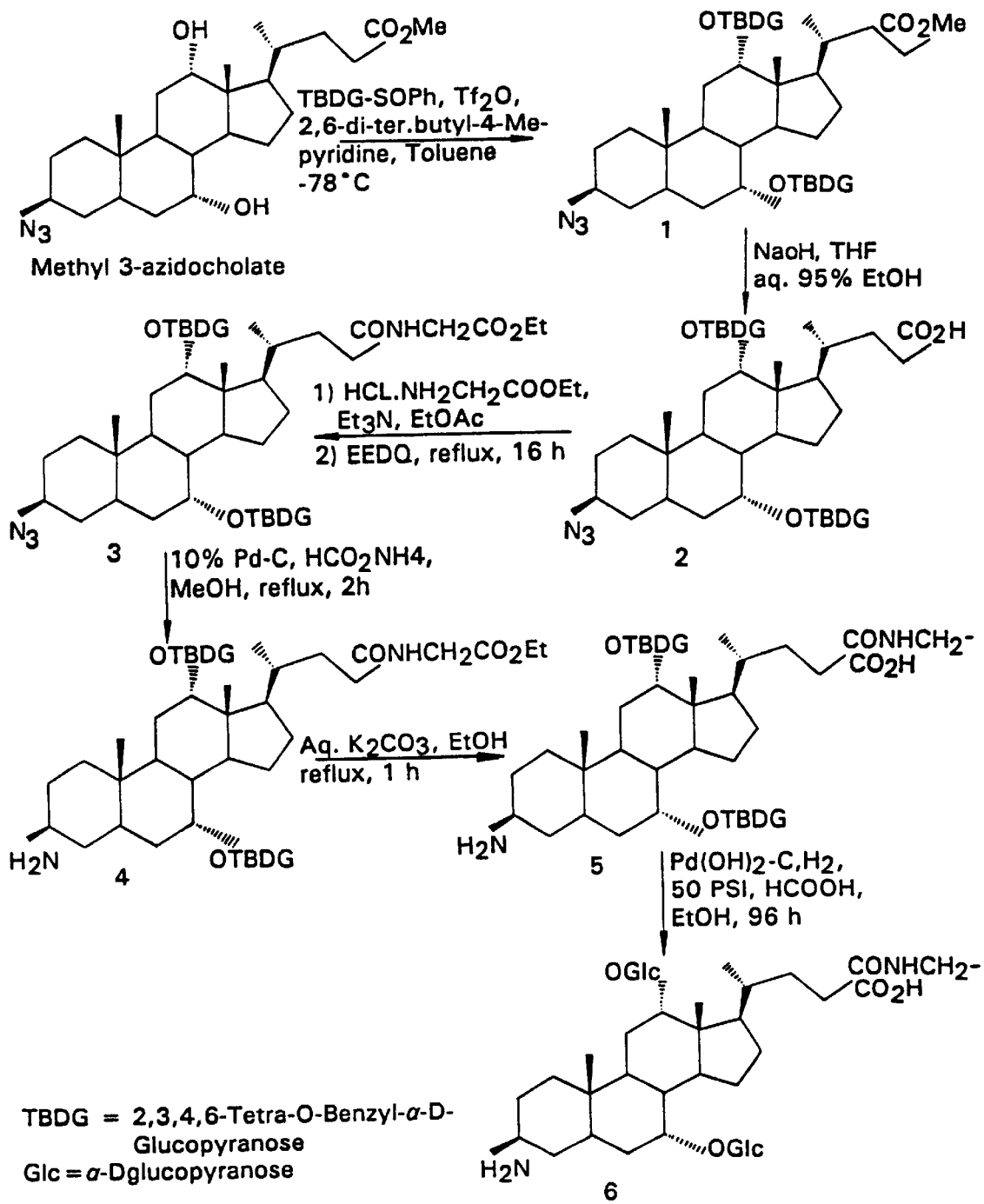
FIG. 1. Synthetic scheme for the preparation of 3β-amino-7α,12α-di(1'α-glucosyl)-5β-cholan-25-oic acid N-[carboxymethyl]amide.

In the process of the present invention, a cholic acid ester compound is converted to an intermediate bearing a leaving group at the 3-position of the steroid nucleus. In a specific embodiment, the leaving group is chosen from among a tosylate or a mesylate. Thus, methyl cholic acid ester is treated in dry pyridine with a slight excess of methanesulfonyl chloride to provide the 3-mesylate intermediate. The 3-tosyloxy intermediate is obtained, likewise, using a slight excess of p-toluenesulfonyl chloride.

The hydroxy groups at C-7 and C-12 do not react with the sulfonyl chloride reagent under appropriate conditions (e.g., at 0° C.). Large excesses of sulfonyl chloride reagent should be avoided, nonetheless, as C-7 by products can be observed, especially with the tosyl chloride reagent.

Other solvents for the reaction include, but are not limited to, methylene chloride and methylene chloride/pyridine mixtures, optionally, in the presence of a small amount of dimethylaminopyridine.

Subsequently, the leaving group is displaced by an azido group with inversion of the stereochemistry at C-3 to provide the 3-azido-substituted cholic acid ester. Thus, the 3-mesylate or 3-tosylate is treated with sodium azide, preferably in excess. Suitable solvents include, but are not limited to, dimethylsulfoxide, dimethylformamide, N-methylpyrrolidone, and the like. The reaction is typically carried out at elevated temperature.

In a specific embodiment of the invention, 1.5 equivalents of sodium azide is added at room temperature to 1.0 equivalents of methyl 3-tosylcholate in DMSO. Preferably, the reaction is carried out at elevated temperature. Hence, the resulting mixture is heated to about 90° C. and stirred for ca. 2 h. After workup, the methyl 3-azidocholate is isolated as a white crystalline solid.

This 3-azido intermediate is then glycosylated at the open hydroxyl groups using the glycosyl sulfoxide chemistry first described by Kahne, D. et al. in *J. Am. Chem. Soc.* (1989) 111:6881–6882. Additional guidance on the glycosylation step can be found in International Publication No. WO 93/11772. The complete disclosures of these publications are incorporated by their reference herein. Typically, the 3-azido cholic acid ester is dissolved in toluene, mixed with the desired glycosyl sulfoxide, and treated with an activating agent, such as triflic anhydride to initiate the condensation reaction. The reaction temperature can be chosed over a wide range, e.g., ca. −78° C. to ca. 20° C., preferably, ca. −40° C. to ca. 0° C.

As mentioned above, and described in greater detail in the Examples section, the glycosylation step can be carried out on the 3-tosyl or 3-mesyl intermediate, followed by the nucleophilic displacement step using sodium azide.

In any event, reduction of the 3-azido-substituted glycosylated cholic acid ester derivative is then accomplished in a number of ways, usually with the protecting groups of the sugar moieties in place. For instance, reduction to give the amine is effected by treating the 3-azido-substituted glycosylated intermediate with ammonium formate and palladium on carbon, triphenyl phosphine or Raney nickel. Reduction can also be effected by treatment with lithium aluminum hydride, although this method is accompanied by reduction of any ester groups present in the starting material.

Figure 4:
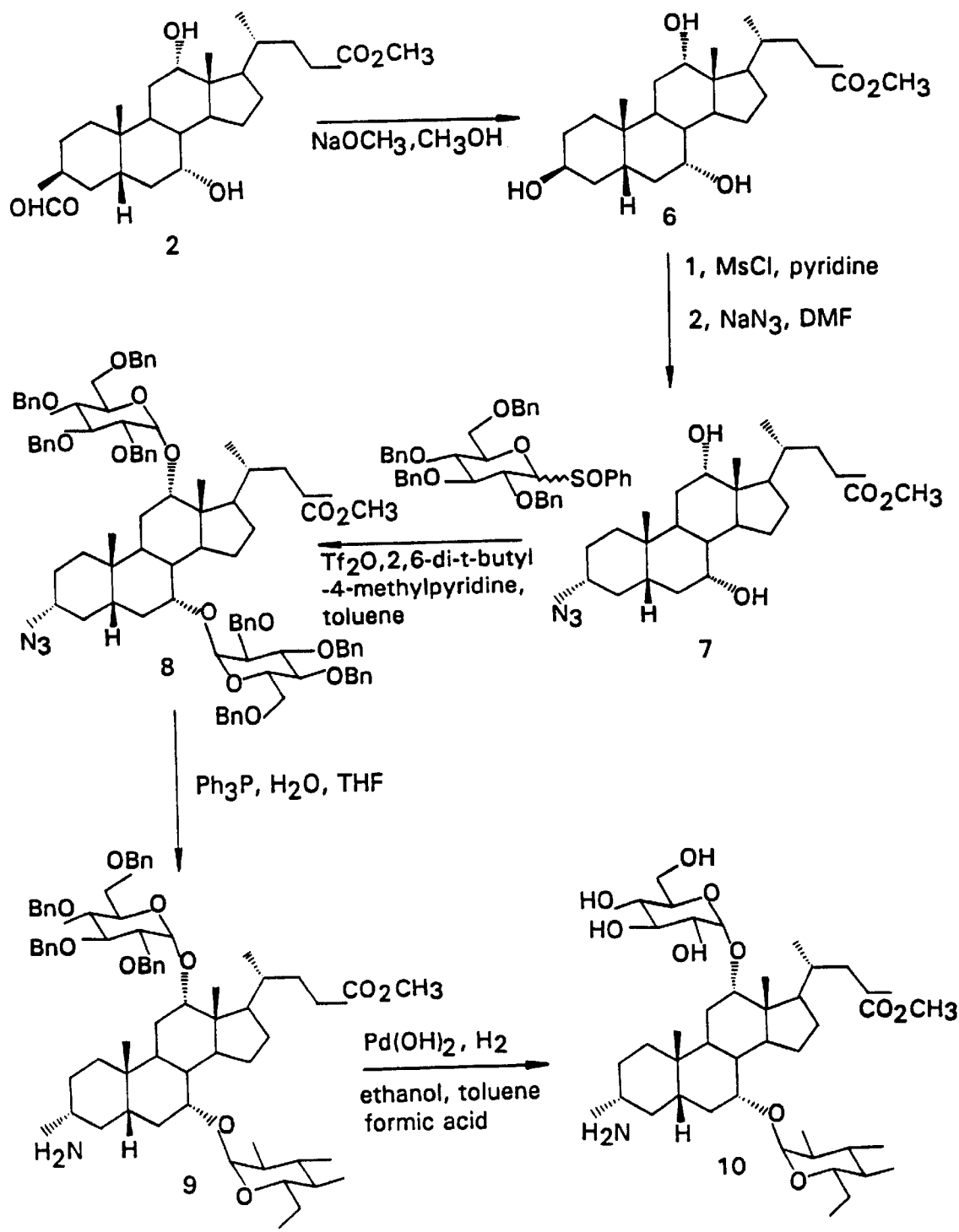
FIG. 4. Synthetic scheme for the preparation of methyl 3α-amino-7α,12α-di(1'α-glucosyl)-5β-cholate.

Useful solvents include aqueous tetrahydrofuran and the like. Preferably, the reaction is carried out at elevated temperature. Thus, for example, a sealable reaction vessel is charged with 0.5 g of the 3-azido compound 8, illustrated in FIG. 4, and dissolved in 6 mL of an ethyl acetate/methanol solvent mixture (2:1, v/v). Wet activated Raney nickel (ca. 1 g) is then added to the vessel, which is then sealed and pressurized with hydrogen to 50 psi. The reaction vessel and its contents are heated to 55° C. for about 1 h.

After cooling, the vessel is depressurized and its contents filtered. The resulting filtrate is concentrated to provide ca. 0.5 g of a colorless oil, identified as the corresponding 3-amino-substituted bisglycosyl cholic acid methyl ester 9, illustrated in FIG. 4.

Subsequently, hydrolysis of the glycosyl protecting groups, typically benzyl, pivaloyl or isopropylidine groups provides the 3-amino-substituted glycosylated bile acid ester derivative which can be purified using reverse phase column chromatography. Hydrolysis can be effected by treatment of the protected glycoside with palladium hydroxide on carbon in a protic medium (e.g., an ethanol/toluene solvent mixture in the presence of formic or acetic acid), followed by hydrogenolysis.

The reduction/deprotection steps can also be carried out in a single step, if desired. Hence, 3-azido-substituted glycosylated intermediate is dissolved in an acidic protic solvent mixture comprised, e.g., of concentrated hydrochloric acid, tetrahydrofuran, and methanol. Hydrogenation over a metal catalyst, such as palladium on activated carbon provides the debenzylated 3-aminoglucosylcholic acid alkyl ester product as the hydrochloric acid addition salt.

In a preferred embodiment of the present invention, the 3-amino product is purified by elution through an MCI CHP-20P reverse-phase gel column (available from Mitsubishi Chemical) using an aqueous methanol eluent (e.g., a gradient of 0–50% methanol in water or an isocratic solution of 25% methanol in water). The final product is isolated from the chromatography solvent under reduced pressure and preferably freeze-dried to provide the pure solid.

In a further development, protected aryl thiosugars are prepared from inexpensive peracetylated sugars as starting materials. For example, a phenyl tetrabenzylthioglucose (4) is synthesized according to the scheme, below, in which α,β-D-glucose pentaacetate is treated with thiophenol in the presence of a catalytic amount of boron trifluoride etherate in dichloromethane solvent.

From a scale-up point of view, the concern involved with the handling of toxic, stenchy thiophenol can be eliminated substantially with the use of a completely closed cannula system in which thiophenol is pumped directly into the reaction mixture without any exposure to the atmosphere. In addition, it has been found that noxious odors during work-up can be greatly reduced by using only a sight excess (e.g., 1.1 equivalents) of thiophenol. Indeed, the use of equimolar amounts of sugar and thiophenol does not adversely effect reaction yield.

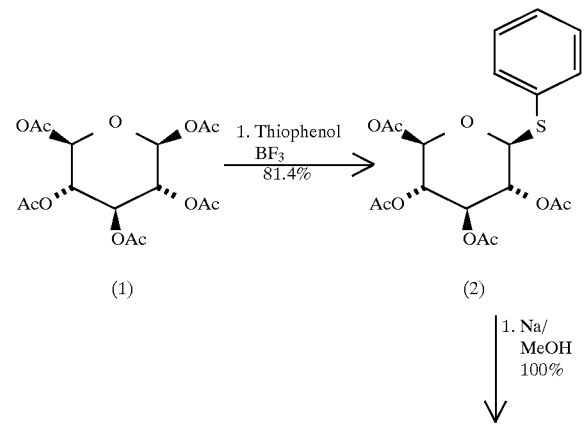

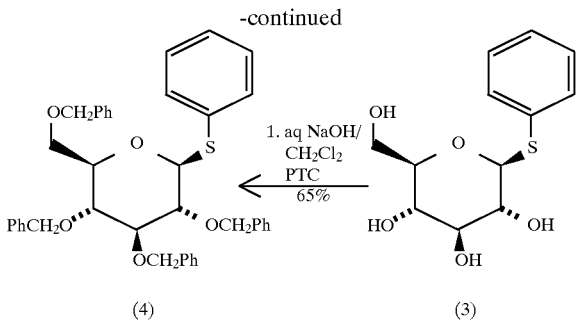

(4)    (3)

Prior procedures call for 1.5 equivalents of borontrifluoride. It is has been found surprisingly that one-half equivalent of $BF_3$ provides excellent results.

With only minimal purification (See, e.g., Examples section), intermediate (2) is deacetylated by treatment with catalytic sodium methoxide in methanol under anhydrous conditions to give the corresponding phenyl 1-thio-β-D-glucoside (3) in quantitative yield with 98.3% HPLC purity.

Intermediate 3 is fully benzylated under phase transfer conditions using a modification of a literature procedure: *J. Carb. Chem.* (1994) 13(2):141–161, incorporated by reference herein in its entirety.

Similarly, other protecting groups can be used, including, but not limited to, pivaloyl, isopropylidine, trimethylsilyl, tert-butyldimethylsilyl, tert-butyldiphenylsilyl, triisopropylsilyl, acetyl, tetrahydropyranyl, benzoyl, benzylidene, (2-methoxyethoxy)methyl, orthoester, paramethoxybenzyl, allyl groups, and the like.

By the same token, other sugar moieties can also be utilized in the three-step process of the invention. Examples of such sugar moieties include, but are not limited to, hexoses, deoxyhexoses, furanoses, and deoxyfuranoses. In particular, these sugars may be selected from natural (D-isomer) or unnatural (L-isomer) allose, altrose, glucose, mannose, gulose, idose, galactose, talose, ribose, arabinose, xylose, lyxose, and the like.

Recrystallization from methanol provides pure (96% HPLC) 4 in 65% yield which is exclusively in the β form.

Accordingly, the methods disclosed herein provide a number of 3-amino-substituted glycosylated bile acid derivatives and intermediates to their synthesis, including cholic acid, allocholic acid, deoxycholic acid or chenodeoxycholic acid derivatives, depending on the starting material. Specific intermediates of note, include the 3β-azido-7α,12α-di(1'α-glucosyl) -5β-cholic acid, its salt, ester or amide or the compound 3α-azido-7α,12α-di(1'α-glucosyl) -5β-cholic acid, its salt, ester or amide.

Furthermore, a novel difluoro cholane derivative is also disclosed, 3β,25-difluoro-7α,12α-di(1'α-glucosyl)-5β-cholane. It is believed that this compound will exhibit permeation enhancing characteristics and, thus, will be useful in facilitating the penetration of diagnostic, prophylactic or therapeutic agents across biological or synthetic membranes, particularly, mucosal membranes.

In addition, FIG. 9 lists selected solvents or solvent mixtures from which various reagents, intermediates or products described herein may be recrystallized to provide purer compounds.

As a further illustration of the present invention, the following examples are provided, which describe in further detail the general aspects of the present process.

EXAMPLES

1. Synthesis of 3β-Amino-7α-12α-di(1'α-glucosyl)-5β-cholan-24-oic Acid N-[Carboxymethyl]amide (6) (See, FIG. 1).

Reactions are generally run under a positive pressure of dry nitrogen. Anhydrous solvents are used unless water is involved in the reaction. Flash chromatography employs Merck silica gel (Kieselgel 60, 200–400 mesh). TLC is performed with 0.2 mm coated commercial silica gel plates (E. Merck, Kieselgel 60 $F_{254}$). Melting points are determined using a Mul-Temp 11 (Laboratory Devices) capillary-melting-point apparatus in open capillary tubes and are uncorrected. Microanalysis are performed by Atlantic Microlab, Inc., Norcross, Ga. Infrared Spectra are recorded on Midac Prospect-IR(FT-IR) and reported in wavenumbers ($cm^{-1}$). Proton NMR spectra are measured at 300 MHz on a Varian instrument. Chemical shifts are reported in ppm downfield from TMS.

1.1. Methyl 3β-Azido-5β-cholate

A mixture of methyl 3-O-mesylcholate (40 g, 80 mmol) and sodium azide (26 g, 400 mmol) in 2-methylpyrrolidone (200 mL) is heated at 105° C. for 3 h. Afterward the reaction mixture is poured into ice-cold water and stirred for 15 min. After filtration, the solids are washed with water (1 L) and air dried. Recrystallization of the precipitate from methanol (125 mL) gives 32.18 g (90%) of methyl 3-azidocholate as white needles (mp 148°–149° C.). TLC (solvent—EtOAC:Hexane=3:2) $R_f$=0.5. IR (KBr): 3448, 2938, 2868, 2097, 1730 $cm^{-1}$. $^1H$ NMR ($CDCl_3$): δ 4.05 (S, 1h), 3.95 (D, 1h), 3.67 (S, 3h), 2.62–0.70 (m, 36h). Fab MS 470 $(M+Na)^+$.

1.2. Methyl 3β-Azido-7α,12α-di(2',3',4',6'-tetra-O-benzyl-1'α-glucosyl)-5β-cholate (1)

Triflic anhydride (9.24 mL, 55 mmol) is added to cooled (−78° C.) toluene (100 mL) solvent with stirring for 5 min. To this solution, dried (by azeotropic distillation from toluene) phenyl 2,3,4,6-tetra-O-benzyl-D-glucopyranosyl-1-sulfoxide (32.43 g, 50 mmol), dissolved in toluene (100 mL), is added dropwise. After 15 min of stirring, a solution of dried (by azeotropic distillation from toluene) 2,6-diterbutyl-4-methyl-pyridine (3.21 g, 40 mmol) in toluene (20 mL) is added to the reaction mixture and stirred for 10 min at −78° C. To this reaction mixture, dried (by azeotropic distillation from toluene) methyl 3-azidocholate (8.94 g, 20 mmol) in $CH_2Cl_2$ and toluene (1:4, 50 M1) is added dropwise. The reaction progress is monitored by TLC. The temperature of the reaction mixture is slowly allowed to rise to −60° C. over 45 min. During this time, the TLC spot due to methyl 3-azidocholate completely disappears. The reaction mixture is then poured into saturated aqueous sodium bicarbonate (250 mL) and stirred for 10 min. The organic layer is separated, and the aqueous layer is extracted with dichloromethane (2×50 mL). The organic layers are combined and washed with water (3×250 mL), dried ($Na_2SO_4$), and concentrated. The residue is purified by flash chromatography (EtOAC:Hexane=1:9 to 1:4) to furnish 1 (12 g, 40%), which is immediately recrystallized (EtoAC:Hexane= 1.5) to give 9 g (30%) of product as needles (mp 112°–114° C.). TLC (solvent—EtOAC:Hexane=1:4) $R_f$=0.6. IR (KBr): 3085, 3061, 3029, 2921, 2867, 2097, 1735, 1603, 1495, 1452, 1360, 1256, 1207, 1160, 1091, 1071, 1031 $cm^{-1}$. $^1H$ NMR ($CDCl_3$): δ 7.37–6.84 (m, 4OH), 5.15 (d, 1H, J=4 Hz), 4.95 (d, 1H, J=4 Hz), 4.86–4.26 (m, 15H), 4.08–3.40 (m, 16H), 2.60–0.71 (m, 36H). Fab MS: 1515 $(M+Na)^+$. Anal. Calc. for $C_{93}H_{110}O_{14}N_3$: C, 74.76; H, 7.43; N, 2.81. Found: C, 74.84; H, 7.40; N, 2.79.

1.3. 3β-Azido-7α,12α-di(2',3',4',6'-tetra-O-benzyl-1'α-glucosyl)-5β-cholan-24-oic acid (2)

To a stirred solution of 1 (4.1 g, 2.75 mmol) in THF (50 mL), is added NaOH (1.1 g, 27.5 mmol) in 95% aqueous ethanol (50 mL). The mixture is heated under reflux for 1.5 h. The mixture is then allowed to cool and is concentrated to provide a residue, which is dissolved in ethyl acetate (100 mL), washed consecutively with water (2×50 mL), saturated aqueous sodium bicarbonate (2×50 mL), and brine (100 mL). After drying (Na$_2$SO$_4$), the solvent is evaporated to afford pure 2 (3.86 g, 95%) as a white foam (mp 60°–62° C.). TLC (solvent—EtOAC:Hexane=3.7) R$_f$=0.2. IR (KBr); 3420, 3080, 3057, 3030, 2922, 2868, 2097, 1735, 1725, 1707, 1496, 1451, 1362, 1273, 1147, 1070 cm$^{-1}$. $^1$H NMR (CDCl$_3$): δ 7.20–6.85 (m, 40H), 5.03 (d, 1H, J=3 Hz), 5.02 (d, 1H, J=3 Hz), 4.85–3.20 (m, 28H), 2.62–0.77 (m, 36H). Fab MS: 1502 (M+Na)$^+$. Anal. Calc. for C$_{92}$H$_{108}$O$_{14}$N$_3$: C, 74.66; H, 7.36, N, 2.84. Found: C, 74.68; H, 7.18; N, 2.79.

1.4. 3β-Azido-7α,12α-di(2',3',4',6'-tetra-O-benzyl-1'α-glucosyl)-5β-cholan-24-oic Acid N-[Ethyl methylcarboxylate]amide (3)

To a suspension of ethylglycine hydrochloride (420 mg, 3 mmol) in ethyl acetate (100 mL) is added triethylamine (3 mL) with stirring at 40° C. for 1 h. The compound 2 (2.986 g, 2 mmol) and ethyl 1,2-dihydro-2-ethoxy-1-quinolinecarboxylate (EEDQ) (988 mg, 4 mmol) in ethylacetate (100 mL) are then added to this mixture, which is then heated under reflux for 16 h. Afterward, the mixture is cooled, washed successively with 0.5N aqueous NaOH (100 mL), 0.5N aqueous HCl (100 mL), and water (2×200 mL). After drying (Na$_2$SO$_4$), the solvent is evaporated. The residue is purified by flash chromatography (EtOH:CH$_2$Cl$_2$= 1:10) to give 3 (2.66 g, 85%) as a white foam (mp 46°–47° C.). TLC (solvent—EtOH:CH$_2$Cl$_2$=1:19) R$_f$=0.3. IR (IBr): 3410, 3351, 3088, 3060, 3032, 2924, 2098, 1746, 1674, 1503, 1454, 1366, 1262, 1050 cm$^{-1}$. $^1$H NMR (CDCl$_3$): δ 7.25–6.85 (m, 40H), 5.82 (brs, 1H), 5.15 (m, 2H), 4.84–3.40 (m, 30H), 2.60–0.65 (m, 39H). Fab MS: 1586 (M+Na)$^+$. Anal. Calc. for C$_{96}$H$_{115}$O$_{15}$N$_4$: C, 73.67; H, 7.41; N, 3.88. Found: C, 73.45; H, 7.46; N, 3.60.

1.5. 3β-Amino-7α,12α-di(2',3',4',6'-tetra-O-benzyl-1'α-glucosyl)-5β-cholan-24-oic Acid N-[Ethyl methylcarboxylate]amide (4)

To a solution of compound 3 (2.35 g, 1.5 mmol) in ethylacetate (40 mL) and methanol (60 mL) is added ammonium formate (1.26 g, 20 mmol) and 10% palladium on carbon (anhydrous, 200 mg). The contents of the reaction vessel are heated under reflux for 6 h. After filtration through Celite® (15 g), the filtrate is concentrated, dissolved in methylene chloride (100 mL), and washed with water (200 mL). After drying (Na$_2$SO$_4$), the solution is concentrated. The residue is separated into its components by flash chromatography: starting material 3 (500 mg, using 5% ethanol in methylene chloride) and, with 10% ethanol in methylene chloride, product 4 (1.155 g, 50%) as a white foam (mp 64°–66° C.). TLC (solvent—EtOH:CH$_2$Cl$_2$=1:9) R$_f$=0.3. IR (KBr): 3426, 3358, 3090, 3065, 3045, 3012, 2925, 2869, 1741, 1670, 1613, 1520, 1454, 1363, 1321, 1211, 1157, 1085 cm$^{-1}$. $^1$H NMR (CDCl$_3$): δ 7.27–6.90 (m, 40H), 5.81 (brs, 1H), 4.99 (brs, 2H), 4.85–3.40 (m, 25H), 3.24–3.18 (m, 1H), 3.10–3.02 (brs, 1H), 2.92–2.88 (m, 1H), 2.60–0.60 (m, 39H). Fab MS: 1559 (M+Na)$^+$. Anal. Calc. for C$_{96}$H$_{117}$O$_{15}$N$_2$: C, 74.91; H, 7.67; N, 1.82. Found: C, 74.74; H, 7.64; N, 1.86.

1.6. 3β-Amina-7α,12α-di-(2',3',4',6',-tetra-O-benzyl-1'α-glucosyl)-5β-cholan-24-oic Acid N-[Carboxymethyl]amide (5)

To a refluxing solution of compound 4 (770 mg, 0.5 mmol) in ethanol (25 mL), 10% aqueous potassium carbonate (1 mL) is added. Heating under reflux is continued for an additional 1 h. The mixture is concentrated and diluted with methylene chloride (50 mL). The organic layer is washed with water (2×50 mL) and dried (Na$_2$SO$_4$). Evaporation of the solvent furnished 5 (683 mg, 90%) as a white powder (mp 150°–152° C.). TLC (solvent—EtOH:CH$_2$Cl$_2$–1:9) R$_f$=0.1. IR (KBr): 3414, 3086, 3061, 3030, 2923, 2868, 1659, 1640, 1628, 1601, 1497, 1452, 1387, 1159, 1088, 1070, 1028 cm$^{-1}$. $^1$H NMR (CDCl$_3$): δ 7.35–6.85 (m, 40H) 6.20 (br s, 1H), 5.10–3.48 (m, 32H), 3.00–0.60 (m, 36H). Fab MS: 1531 (M+Na)$^+$. Anal. Calc. for C$_{94}$H$_{113}$O$_{15}$N$_2$: C, 74.71, H, 7.54; N, 1.85. Found: C, 74.58; H, 7.76; N, 1.90.

1.7. 3β-Amino-7α,12α-di(-1'α-glucosyl)-5β-cholan-24-oic Acid N[Carboxymethyl]amide (6)

To a solution of 5 (605 mg, 0.4 mmol) in ethanol (100 mL), formic acid (1.5 mL) and palladium hydroxide (20%) on carbon (600 mg) are added. The resulting mixture is hydrogenated at 50 psi for 24 h. TLC indicates incomplete hydrogenolysis. Additional formic acid (1.5 mL) is added and hydrogenation is allowed for another 24 h. Additional formic acid and further hydrogenation can be added and performed as warranted. The reaction mixture is then filtered through sand and a membrane filter and concentrated. The residue is precipitated with EtOAc and filtered. The precipitate is dissolved in 25 mL deionized water and freeze-dried. Reverse-phase column chromatography of the residue over CHP-20 (water followed by MeOH:Water=1:1) gives 189 mg (60%) of 6 as a white foam (mp >275° C., decomp.). TLC (solvent MeOH:CH$_2$Cl$_2$:isopropylamine=2:2:1) R$_f$–0.15. IR (IBr) 3394, 2932, 2878, 2870, 1640, 1630, 1619, 1598, 1389, 1150, 1023 cm$^{-1}$. $^1$HNMR (D$_2$O): δ 5.35–5.33 (m, 1H), 5.08 (d, 1H, J=3 Hz), 4.87 (d, 1H, J=3 Hz), 3.98 (br s, 1H), 3.80–3.24 (m, 14H), 2.60–0.65 (m, 37H). Fab MS: 781 (M+Na)$^+$. Anal. Calc. for C$_{38}$H$_{64}$O$_{15}$N$_2$.3H$_2$O: C, 54.13; H, 8.37; N, 3.32. Found: C, 54.35; H, 8.43; N, 3.25.

Figure 2:
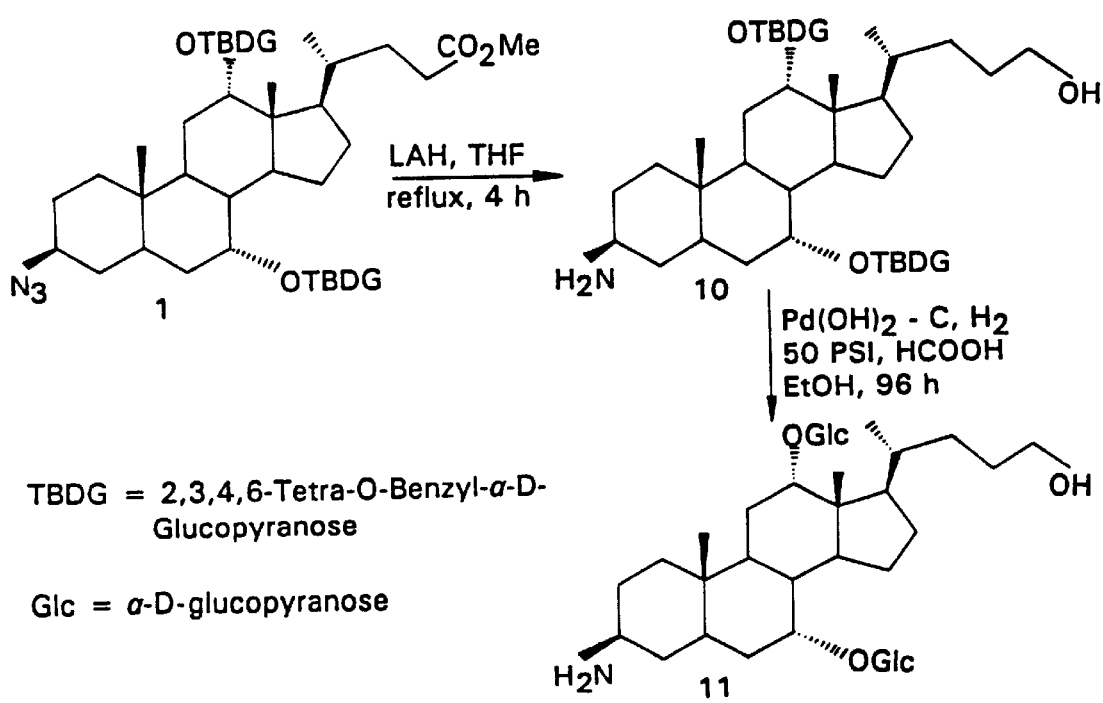
FIG. 2. Synthetic scheme for the preparation of 3β-amino-24-hydroxy-7α,12α-di(1'α-glucosyl)-5β-cholane.

2. Synthesis of 3β-Amino-24-hydroxy-7α,12α-di (1'α-glucosyl)-5β-cholane (11) (See, FIG. 2)

2.1. β-Amino-24-hydroxy-7α,12α-di(1'α-glucosyl)-5β-cholane (10)

To a mixture of lithium aluminum hydride (LAH, 0.19 g, 5 mmol) in anhydrous tetrahydrofuran (THF, 100 mL) is added dropwise at r.t. a solution of compound 1 (7–45 mg, 0.5 mmol) in THF (20 mL). The resulting reacting mixture is heated under reflux for 16 h, and then allowed to cool to r.t. Excess LAH is destroyed by the dropwise addition of aqueous sodium hydroxide (5 mL). The mixture is then acidified with 1N hydrochloric acid (7 mL) and extracted with methylene chloride (2×20 mL). The organic layer is washed with water (2×40 mL), dried (Na$_2$SO$_4$) and concentrated. The residue is purified by flash column chromatography (ethyl acetate:hexane=1:2) to provide 485 mg (70%) of 10 as a white foam (mp 54°–56° C.). TLC (solvent—EtOH:CH$_2$Cl$_2$=1:9) R=0.3. IR (KBr): 3087, 3063, 3030, 2921, 2865, 1454, 1160, 1070 cm$^{-1}$. $^1$H NMR (CDCl$_3$): δ 7.38–6.85 (m, 40H), 5.06 (br d, 2H), 4.95–3.40 (m, 28H), 3.11 (br s, 1H), 2.62–0.72 (m, 39H). Fab MS: 1438 (M+H)$^+$. Anal. Calc. for C$_{92}$H$_{112}$O$_{13}$N: C, 76.73; H, 7.85; N, 0.97. Found: C, 76.38; H, 7.90; N, 0.97.

2.2. 3β-Amino-24-hydroxy-7α,12α-di(1'α-glucosyl)-5β-cholane (11)

Compound 10 (431 mg, 0.3 mmol) is hydrogenated by methods similar to those described above to give 129 mg (60%) of 11 as a white foam (mp 196°–198° C.). TLC (solvent—MeOH:CH$_2$Cl$_2$:Isopropylamine=2:2:1) R$_f$=0.15. IR (KBr): 3399, 2936, 22878, 2869, 1630, 1597, 1590, 1045, 1022 cm$^{-1}$. $^1$H NMR (D$_2$O): δ 5.04 (d, 1H, J=3.6 Hz), 4.82 (d, 1H, J=3 Hz), 3.94 (br s, 1H), 3.74–3.22 (m, 12H), 2.47 (dd, 1H, J=12 Hz and 4 Hz), 2.20 (m, 2H), 1.95–0.90 (m, 36H). Fab MS: 719 (M+H)$^+$. ANal. Clc. for C$_{36}$H$_{63}$O$_{13}$N.4H$_2$O: C, 54.72; H, 9.06; N, 1.77. Found: C, 54.52; H, 8.75, N, 1.67.

Figure 3:
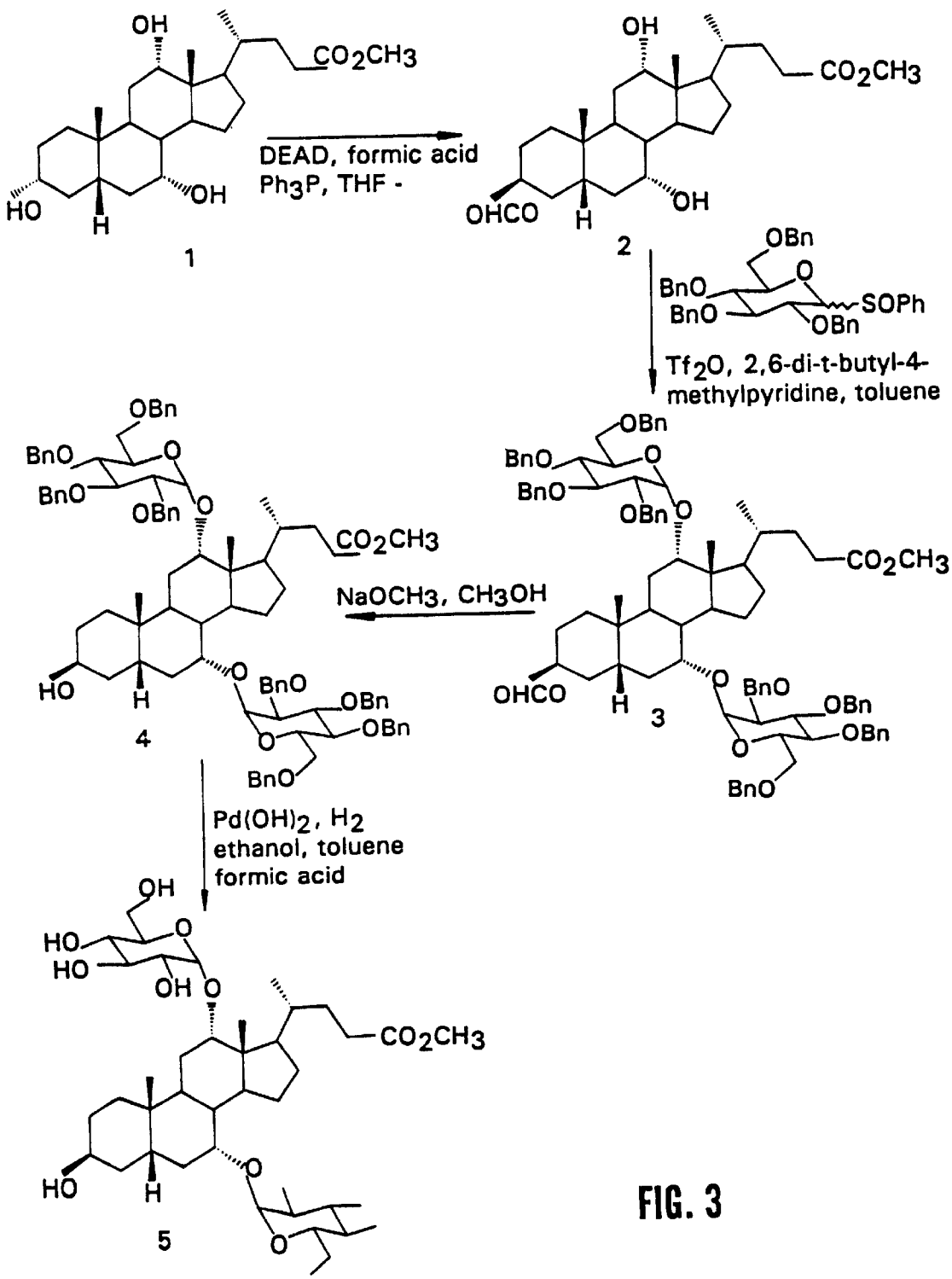
FIG. 3. Synthetic scheme for the preparation of methyl 3β-hydroxy-7α,12α-di(1'α-glucosyl)-5β-cholate.

3. Synthesis of Methyl 3β-Hydroxy-7α,12α-di(1'α-glucosyl)-5β-cholate (5) (See, FIG. 3)

Kiesegel 60 F-254 TLC plate is used for all the TLC work unless otherwise indicated. FT-IR is performed on MIDAC Prospect IR instrument. NMR is performed on Varian VXR300s 300 MHz instrument. Chemical reagents are purchased from Aldrich or Fisher. Dry toluene is distilled from $CaH_2$. All other solvents are used directly from original container without further purification.

3.1. Methyl 3β-O-Forinylcholate (2)

To a solution of methyl cholate 1 (2.11 g, 5 mmol), formic acid (96%, 350 mg) and triphenyl phosphine (1.57 g, 6.0 mmol) in THF (75 mL) is added diethyl azodicarboxylate (DEAD, 1.05 g, 6.0 mmol) at room temperature (r.t.). The reaction mixture is stirred at r.t. for 16 h. Solvent is removed by evaporation. The residue is purified by use of a flash column (50%~60% ethyl acetate in hexane) to give 1.8 g (80%) of 2 as a thick oil: $R_f$ (60% ethyl acetate in hexane) 0.43; $^1H$ NMR δ (CDCl$_3$) 0.76 (s, 3H), 0.99 (s, 3H), 1.12 (d, 3H), 1.2–2.6 (m, 24H), 3.66 (s, 3H), 3.87 (s, 1H), 3.99 (s, 1H), 5.15 (s, 1H), 8.04 (s, 1H).

3.2. Methyl 3β-O-Formyl-7α,12α-O-di(1'α-(2',3',4',6'-O-tetrabenzyl)glucosyl)-5β-cholate (3)

To a solution of phenyl 2,3,4,6,-O-tetrabenzylgluco-1-sulfoxide (6.33 g, 9.8 mmol) in 150 mL dry toluene is added triflic anhydride (1.66 mL, 9.8 mmol) at −78° C. After 15 min. stirring at −78° C., 2,6-di-tbutyl-4-methylpyridine (2 g, 9.8 mmol) in a small amount of toluene is added, followed by 2 (2 g, 4.4 mmol) in a small amount of methylene chloride. The dry ice/acetone bath is then replaced with a dry ice/chloroform bath to keep the reaction temperature at about −60° C. with stirring for 2.5 h. Saturated aq. NaHCO$_3$ (100 mL) is then added. The reaction mixture is extracted with ethyl acetate (3×30 mL). The organic layer is dried and purified by flash column chromatography (20% ethyl acetate in hexane) to give 3 g (44%) of 3 as a thick oil: $R_f$ (20% ethyl acetate in hexane) 0.32; IR (neat) 3031, 2922, 1728, 1710, 1454 cm$^{-1}$; $^1H$ NMR δ (CDCl$_3$) 0.72 (s, 3H), 0.96 (s, 3H), 0.97 (d, 3H), 1.2–2.5 (m, 24H) 3.4–5.2 (m, 30H), 3.62 (s), 7.0–7.4 (m, 40H), 8.02 (s, 1H).

3.3. Methyl 3β-Hydroxyl-7α,12α-O-di(1'α-(2',3',4',6'-O-tetrabenzyl)glucosyl)-5β-cholate (4)

To a solution of 3 (3 g, 2 mmol) in anhydrous methanol (100 mL) at 0° C. is added sodium methylate (138 mg, 2.6 mmol). The mixture is stirred at r.t. for 2 h. Solvent is evaporated, and the residue is taken in methylene chloride, washed with a small amount of saturated aqueous ammonium chloride, and dried. Flash column chromatography (25% ethyl acetate in hexane) purification gives 750 mg (25%) of 4 as a thick oil: $R_f$ (30% ethyl acetate in hexane) 0.36; $^1H$ NMR δ (CDCl$_3$) 0.73 (s, 3H), 0.97 (s, 3H), 1.02 (d, 3H), 1.2–2.5 (m, 24H), 3.61 (s), 3.4–4.9 (m, 30H), 5.04 (t, 1H), 6.9–7.4 (m, 40H). MS m/e 1489 (M$^+$+Na).

3.4. Methyl 3β-Hydroxyl-7α,12α-O-di(1'α-glucosyl)-5β-cholate (5)

To a solution of 4 (750 mg) in toluene (5 mL) and ethanol (15 mL) is added Pd(OH)$_2$ (20% in carbon, 750 mg) and formic acid (95%, 0.7 mL). The mixture is hydrogenated at 50 psi for 18 h, then filtered. The filtrate is then evaporated. The residue is redissolved in methanol, filtered and evaporated again. The residue is then dissolved in a small amount of water, purified by reverse-phase column chromatography (60 mL MCI CHP-20P gel column; 25% H$_2$O in methanol). Lyophilization gives 260 mg (68%) of 5 as a white solid: $R_f$ (C-18 reverse phase, 30% $_2$H O in methanol) 0.28; mp. 170° C. (recrystallized with methanol-ethyl acetate, phase transfer); IR (KBr) 3430, 2880, 1722, 1439 cm$^{-1}$; $^1H$ NMR (D$_2$O) δ 0.62 (s, 3H), 0.75 (d, J=6.3 Hz), 0.82 (s, 3H), 1.0–2.4 (m), 3.2–3.8 (m), 3.51 (s), 3.92 (s, 2H), 4.81 (d, J=3.6 Hz, 1H), 5.06 (d, J=3.9 Hz, 1H); MS m/e 769 (M$^+$+Na); Anal. Calc. (MW+2 H$_2$O) C, 56.77; H, 7.99; Found C, 56.82; H, 8.22.

4. Synthesis of Methyl 3α-Amino-7α,12α-di(1'α-glucosyl)-5β-cholate (10) (See, FIG. 4)

4.1. Methyl 3β-Hydroxycholate (6)

Anhydrous methanol (10 mL) is added to a mixture of 2 (225 mg, 0.5 mmol) and sodium methylate (35 mg) at 0° C. The solution is stirred at r.t. for 0.3 h. Solvent is evaporated. The residue is taken up in methylene chloride, washed with conc. ammonium chloride, and dried. Removal of solvent gives 170 mg (84%) of 6 as a white solid: $R_f$ (90% ethyl acetate in hexane) 0.11; $^1H$ NMR (CDCl$_3$) δ 0.68 (s, 3H), 0.93 (s, 3H), 0.97 (d, J=6 Hz, 3H); 1.1–2.5 (m, 25H), 3.65 (s, 3H), 3.85 (s, 1H), 3.97 (m, 1H), 4.04 (s, 1H), 6.72 (br.s,).

4.2. Methyl 3α-Azidocholate (7)

To a solution of 6 (2.73 g, 6.4 mmol) in dry pyridine at 0° C. is added methanesulfonyl chloride (0.6 mL, 7.7 mmol). The resulting mixture is stirred at 0° C. for 2 h and r.t. for 2 h. Solvent is evaporated; the residue is taken in methylene chloride, washed with conc. ammonium chloride, and dried. The crude mesylate is dissolved in DMF (40 mL) and treated with NaN$_3$ (2 g). The mixture is stirred while heated to 110° C. for 4 h. Solvent is removed. The residue is taken up in methylene chloride, washed with conc. ammonium chloride, and dried. Flash column chromatography (20 ethyl acetate in hexane) gives 1.15 g (40%) of 7 as a white solid: $R_f$ (30% ethyl acetate in hexane) 0.45; IR (IBr) 3477, 2939, 2092, 1732 cm$^{-1}$; $^1H$ NMR (CDCl$_3$) δ 0.68 (s, 3H), 0.90 (s, 3H), 0.96 (d, J=6.3 Hz, 3H), 1.1–2.5 (m, 24H), 3.14 (m, 1H), 3.66 (s, 3H), 3.85 (d, J=2.7 HJz, 1H), 3.98 (s, 1H).

4.3. Methyl 3α-Azido-7α,12α-O-di(1'α-(2',3',4',6'-O-tetrabenzyl)glucosyl)-5β-cholate (8)

To a solution of phenyl w,e,4,6-O-tetrabenzylgluco-1-sulfoxide (3.7 g, 5.7 mmol) in 120 mL dry toluene is added triflic anhydride (1.05 mL, 9.8 mmol) at −78° C. After 30 min. stirring at −78° C., 2,6-di-tbutyl-4-methylpyridine (1.17 g, 5.7 mmol) in a small amount of toluene is added, followed by 7 (1.15 g, 2.6 mmol) in 10 mL methylene chloride. The reaction mixture is stirred at −78° C. for 0.5 h. The dry ice/acetone bath is replaced with a dry ice/chloroform bath to keep the reaction temperature at about −60° C. for 2.5 h with stirring. 10% aq. NaHCO$_3$ is then added. The reaction mixture is extracted with ethyl acetate (3×50 mL). The organic layer is dried and purified by flash column chromatography (20% ethyl acetate in hexane) to give 1.10 g (28%) of 8 as a thick oil: $R_f$ (25% ethyl acetate in hexane) 0.50; IR (neat) 3030, 2927, 2091, 1736, 1455 cm$^{-1}$; $^1H$ NMR (CDCl$_3$) δ 0.72 (s, 3H), 0.94 (s, 3H), 1.0 (d, 3H), 1.1–2.5 (m, 24H), 3.64 (s), 3.1–5.1 (m, 30H), 6.9–7.4 (m, 40H). MS m/e 1515 (M$^+$+Na+H).

4.4. Methyl 3α-Amino-7α,12α-O-di(1'α-(2',3',4',6'-O-tetrabenzyl)glucosyl)-5β-cholate (9)

The compound 8 (1.1 g, 0.73 mmol) and triphenyl phosphine (0.62 g, 2.3 mmol) are dissolved in THF (30 mL) and H$_2$O (3 mL). The mixture is heated under reflux for 24 h. Solvent is evaporated. The residue is extracted with methylene chloride (3×20 mL) and dried. Flash column chromatography (2–3% methanol in chloroform) gives 640 mg (60%) of 9 as a thick oil: $R_f$ (10% methanol in chloroform) 0.45 (ninhydrin positive; $^1H$ NMR (CDCl$_3$) δ 0.71 (s, 3H), 0.92 (s, 3H), 0.98 (d, 3H), 1.1–2.5 (m, 24H), 3.63 (s), 3.3–5.1 (m, 32H), 6.9–7.4 (m, 40H).

4.5. Methyl 3α-Amino-7α,12α-O-di(1'α-glucosyl)-5α-cholate (10)

To a solution of 9 (640 mg) in 3 mL toluene and 30 mL ethanol is added Pd(OH)$_2$ (20% on carbon, 640 mg) and formic acid (96%, 0.64 mL). The mixture is hydrogenated at 50 psi for 24 h. Then, 0.64 mL additional 96% formic acid is added and the hydrogenation is continued for another 24 h. The mixture is filtered and evaporated. The residue is redissolved in $H_2O$ and the pH of the aqueous solution is titrated to 9 with 10% $Na_2CO_3$. The solution is purified by reverse-phase column chromatography (60 mL MCI CHP-20P gel column; 25% $H_2O$ in methanol) to give 250 mg (77%) of 10 as white solid: $R_f$ (60% methanol, 20% methylene chloride, 20% isopropylamine) 0.25; mp. 190° C. (recrystallized with methanol-ethyl acetate, phase transfer); IR (KBr) 3396, 2938, 1736 $cm^{-1}$; $^1H$ NMR ($D_2O$) δ 0.63 (s, 3H), 0.78 (d, J=6 Hz, 3H), 0.85 (s, 3H), 1.0–2.4 (m, 24H), 2.92 (br. s, 1H), 3.2–3.8 (m), 3.54 (s), 3.94 (s, 2H), 4.84 (d, JJ=4.2 Hz, 1H), 5.05 (d, J=4.2 Hz, 1H), MS m/e 769 ($M^+$+Na+H); Anal. Calc. (MW +$6H_2O$), 52.05; H, 7.44; N, 1.64; Found C, 52.12; H. 7.82; N, 1.64.

5. Synthesis of the Methyl 3β-Amino-7α-(1'α-glucosyl)chenodeoxycholate (5) (See, FIG. 5)

5.1. Methyl 3-O-Methanesulfonylchenodeoxycholate (1)

Methyl chenodeoxycholate (27 g, 61.5 mmol) is dissolved in 100 mL dichloromethane (DCM), pyridine (20 mL). Dimethylaminopyridine (DMAP) (1.22 g, 10 mmol) is then added. The reaction mixture is chilled to 0° C., and methanesul-fonyl chloride (7.5 mL, 11.0 g, 96.7 mmol) is added dropwise. The reaction mixture is heated at 60° C. for 3 h, cooled to r.t., washed with 5% HCl, water, sodium bicarbonate, brine, and dried over sodium sulfate. The solvent is evaporated under reduced pressure (1 mm Hg, 80° C. in a bath) to give mesylate 1 as a thick oil, weight 27 g (90%). This material is used in the next step without further purification.

5.2. Methyl 3β-Azido-chenodeoxycholate (2)

Methyl 3-O-methanesulfonyl-chenodeoxycholate (25 g, 51 mmol) and sodium azide (12 g, 185 mmol) are dissolved in 80 mL of N-methylpyrrolidone and heated at 110° C. (in an oil bath) for 3 h. The reaction mixture is, cooled to r.t. and poured onto 300 g of ice to give an oil. The oil is extracted with toluene and purified by flash column chromatography (EA-Hexane from 0 to 40% of EA) to give substance 2, which crystallized from hexane. Weight 13 g (60%), m.p. 112°–113° C. (methanol). IR: 3380 (υCOOMe). $^1H$ NMR ($CDCL_{32}$) δ 3.62 (s, 3H), 2.4–1.3 (26H), 0.983 (d, 3H), 0.955 (s, 3H), 0.685 (s, 3H).

5.3. Methyl 3β-Azido-7α-O-(tetra-O-benzyl-α-D-glucosyl-1')chenodeoxycholate (3)

Phenyl sulfonyl-tetra-benzyl-D-glucoside (4.05 g, 6.25 mmol) in toluene (150 mL) is treated dropwise at −78° C. with triflic anhydride (1.06 mL, 6.25 mmol) in toluene (10 mL). 2,6-Diisopropyl-4-methyl-pyridine (1.3 g, 6.25 mmol) in toluene (10 mL) is added dropwise. Methyl 3-azido-deoxycholate 2 (2.16 g, 5 mmol) in toluene/dichloromethane (10 mL/10 mL) is added dropwise to the reaction mixture. The procedures are carried out at −78° C. under Ar. After the addition, the stirring is continued 1 h, followed by addition of a saturated solution of sodium bicarbonate (50 mL). The organic layer is washed with 5% HCl, water, brine, and dried over sodium sulfate. Evaporation of the solvent and purification by flash chromatography on silica gel with Ethylacetate (EA)/Hexane (gradient: from 0% to 25% of EA) affords 3.50 g (3.66 mmol, 73% yield) of 3. $R_f$=0.7 (silica, EA/Hexane 2/5), IR (neat) 2108, 1734 $cm^{-1}$; $^1H$ NMR ($CDCl_3$) δ 7.2–7.44 (m, 20H), 4.31–4.45 (m, 15H), 3.62 (s, 3H), 0.850 (d, 3H), 0.671 (s, 3H), 0.649 (s, 3H).

5.4. Methyl 3β-Amino-7β-O-(tetra-benzyl-α-D-glucosyl-1')chenodeoxycholate (4)

The azido derivate 3 (2.8 g, 3 mmol) and triphenylphosphine (1.85 g, 7.0 mmol) are dissolved in THF/water (99 mL/1 mL) and the reaction mixture is heated under reflux with stirring for 24 h. The solvent is removed at reduced pressure; the oil residue is dissolved in EA (50 mL), washed with sodium bicarbonate, then brine, then purified by flash chromatography in DCM/EtOH (gradient from 0% to 20% of EtOH) to give 1.5 g (50% yield) of 4, as a semi-solid: $R_f$=0.10 (silica, EA/Hexane 2/5), IR (neat) 3380, 1740 $cm^{-1}$; $^1H$ NMR ($CDCl_3$), δ 7.15–7.8 (m, 20H), 4.40–5.1 (m, 15H), 3.65 (s, 3H), 0.888 (d, 3H), 0.670 (s, 3H), 0.630 (s, 3H).

5.5. Methyl 3β-Amino-7α-O-(α-D-glucosyl-1') chenodeoxycholate (5)

The aminoderivative 4 (1.2 g, 1.3 mmol) is dissolved in 40 mL of EtOH, and a catalyst (10% $Pd(OH)_2$/C, 0.2 g) and formic acid (1 mL) are added. The reaction mixture is hydrogenated in a 0.5 L Parr® vessel at 50 psig for 48 h. The catalyst is filtered off, and the solvent is evaporated under reduced pressure to give a solid residue. Ethyl acetate (5 mL) is added to crystallize out the product. It is filtered and washed with hexane. Weight 0.27 g (yield 37%), m.p. 260° C. (decomposition). The substance is dissolved in water (5 mL) and freeze dried. $R_f$=0.7 (silica, MeOH/DCM/isopropylamine 60/20/20); IR (KBr)$υ_{cOMe1734,υ}$ OH,NH3280–3440 $cm^{-1}$; $^1H$ NMR ($D_2O$) δ 4.88 (s, 1H), 3.2–3.75 (m, 6H), 3.52 (s, 3H), 0.849 (s, 3H), 0.778 (d, 3H), 0.505 (s, 3H). Anal. Calcd. for $C_{31}H_{52}NO_8$HCOOH: C, 62.5; H, 8.89; N, 2.28%. Found: C59.0; H, 8.80; N, 2.25%. MS: M+$Na^+$. Calcd, 590. Found 590.

6. Synthesis of 3-Amino-12-O-glucosyldeoxycholate (10) (See, FIG. 6)

6.1. 3α-O-Methanesulfonyldeoxycholic Acid, Methyl Ester (6)

Figure 5:
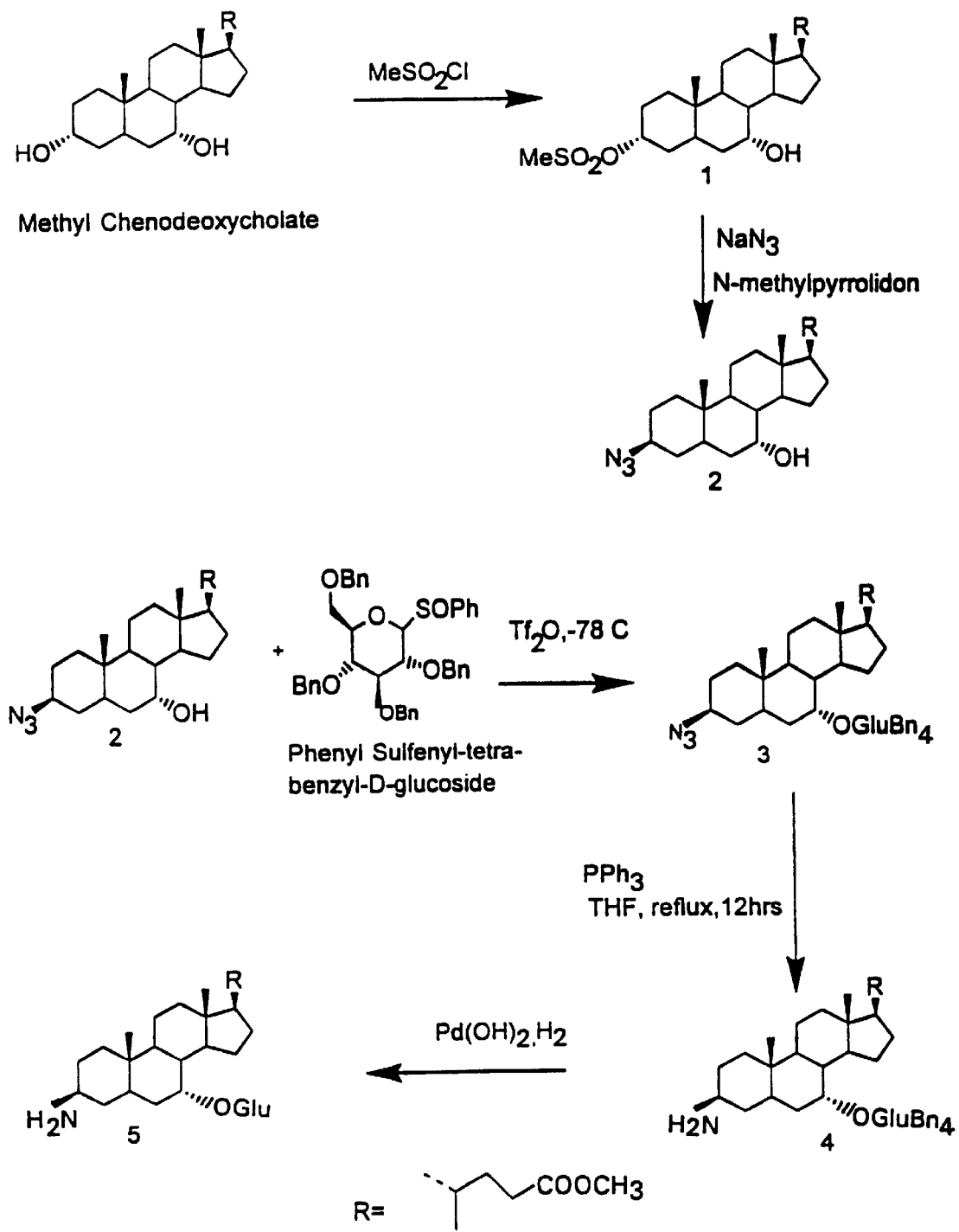
FIG. 5. Synthetic scheme for the preparation of methyl 3β-amino-7α-(1'α-glucosyl)chenodeoxycholate.

The title compound is prepared in the same manner as the methyl 3-O-methanesulfonyl-chenodeoxycholate (1, FIG. 5). It is obtained as an oil and is used in the next step without further purification.

6.2. 3β-Azidodeoxycholic Acid, Methyl Ester (7)

The title compound is prepared in the same manner as the methyl 3-azido-chenodeoxycholate (2, FIG. 5). Yield is 45%, m.p. 128° C. (from methanol). $R_f$=0.6 (silica, EA/Hexane 2/5). IR (KBr) υ3380, $υ_{N3}$2089, $υ_{COOMe}$1734 $cm^{-1}$. $^1H$ NMR ($CDCL_3$) δ 3.62 (s, 3H), 2.4–1.3 (m, 26H), 0.986 (d, 3H), 0.942 (s, 3H), 0.691 (s, 3H).

6.3. Methyl 3β-Azido-12α-O-(tetra-O-benzyl-α-D-glucosyl-1')-deoxycholate (8)

The title compound is prepared in the same manner as substance 3 of FIG. 5. The yield is 40%. $R_f$ 0.75 (silica, EA/Hexane 2/5). IR (neat) 2103, 1742 $cm^{-1}$. $^1H$ NMR ($CDCL_3$) δ 7.23–7.32 (m, 20H), 4.44–4.97 (m, 15H), 3.67 (s, 3H), 0.854 (d, 3H), 0.688 (s, 3H), 0643 (s, 3H).

6.4. Methyl 3β-Amino-12α-O-(tetra-benzyl-α-D-glucosyl-1')-deoxycholate (9)

Figure 6:
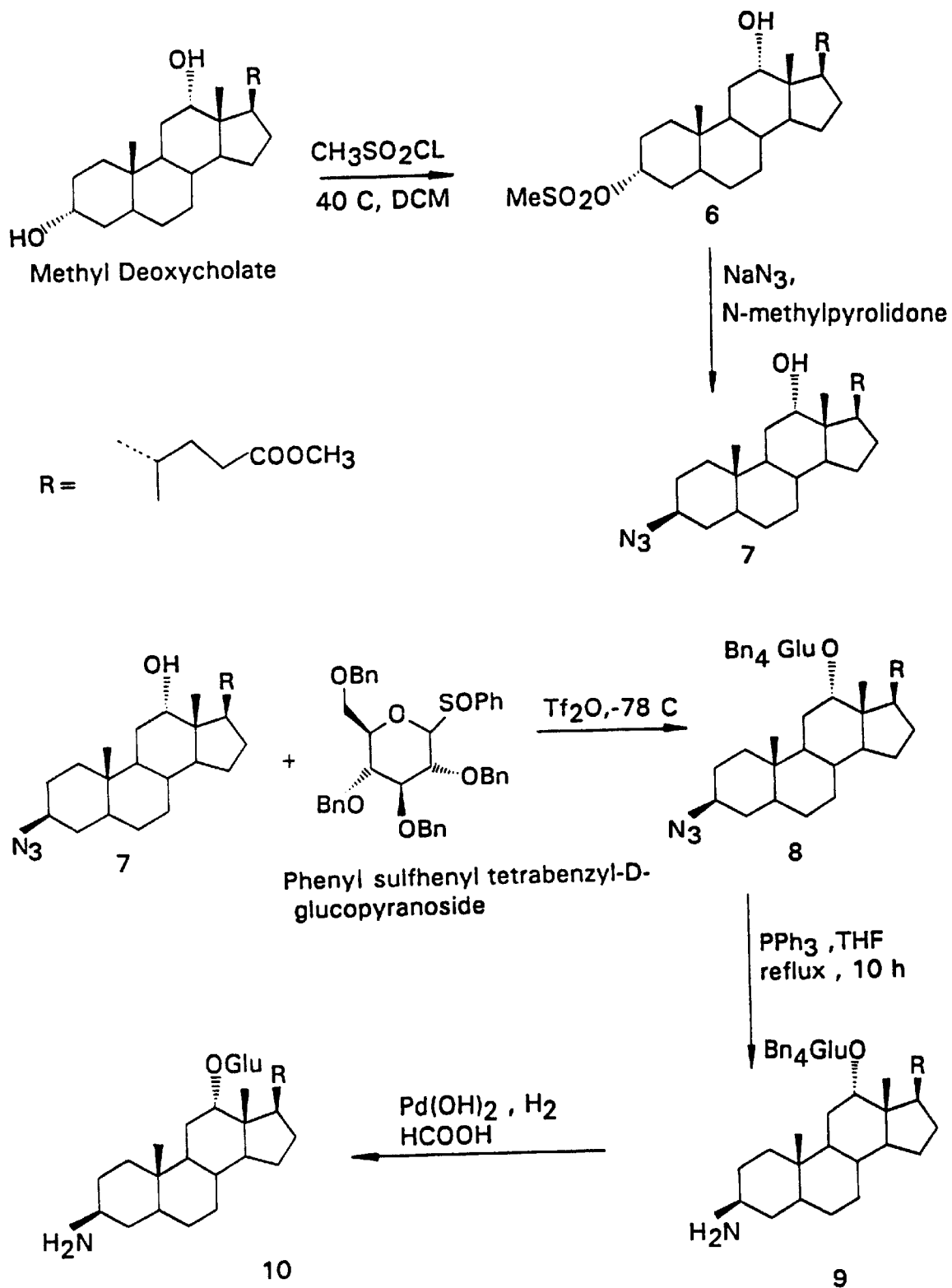
FIG. 6. Synthetic scheme for the preparation of methyl 3β-amino-12α-(1'α-glucosyl)deoxycholate.

The title compound is prepared in the same manner as substance 4 of FIG. 6. The yield is 48%. $R_f$=0.12 (silica, EA/hexane); IR (neat) 1734, 3382 $cm^{-1}$. $^1H$ NMR ($CDCL_3$), 0.867 (d, 3H), 0.676 (s, 3H), 0.628 (s, 3H).

6.5. Methyl 3β-Amino-12α-O-(α-D-glucopyranosyl-1')-deoxycholate (10)

The title compound is prepared in the same manner as a substance 5 of FIG. 5. The yield is 71%, m.p. 250° C. (decomposition). $R_f$=0.7 (silica, DCM/MeOH/i-propylamine 60/20/20). IR (KBr) 3200–3428 $υ_{OH,ny}$, 1734 $υ_{COOMe}$ $cm^{-1}$; $^1H$ NMR ($D_2O$) δ 4.95 (d, 1H), 3.85 (s, 1H), 3.69 (s, 1H), 3.62 (s, 1H), 3.38 (d, 2H), 3.53 (s, 3H), 0.85 (s, 3H), 0.78 (d, 3H), 0.52 (s, 3H) Anal. Calcd. for $C_{31}H_{52}NO_8$.HCOOH; C, 62.5; H, 8.89; N, 2.28%;. Found: C61.5; H, 9.06; N, 2.22%. Mass-spectr: M+$Na^+$. Calcd. 590, Found 590.

Figure 7:
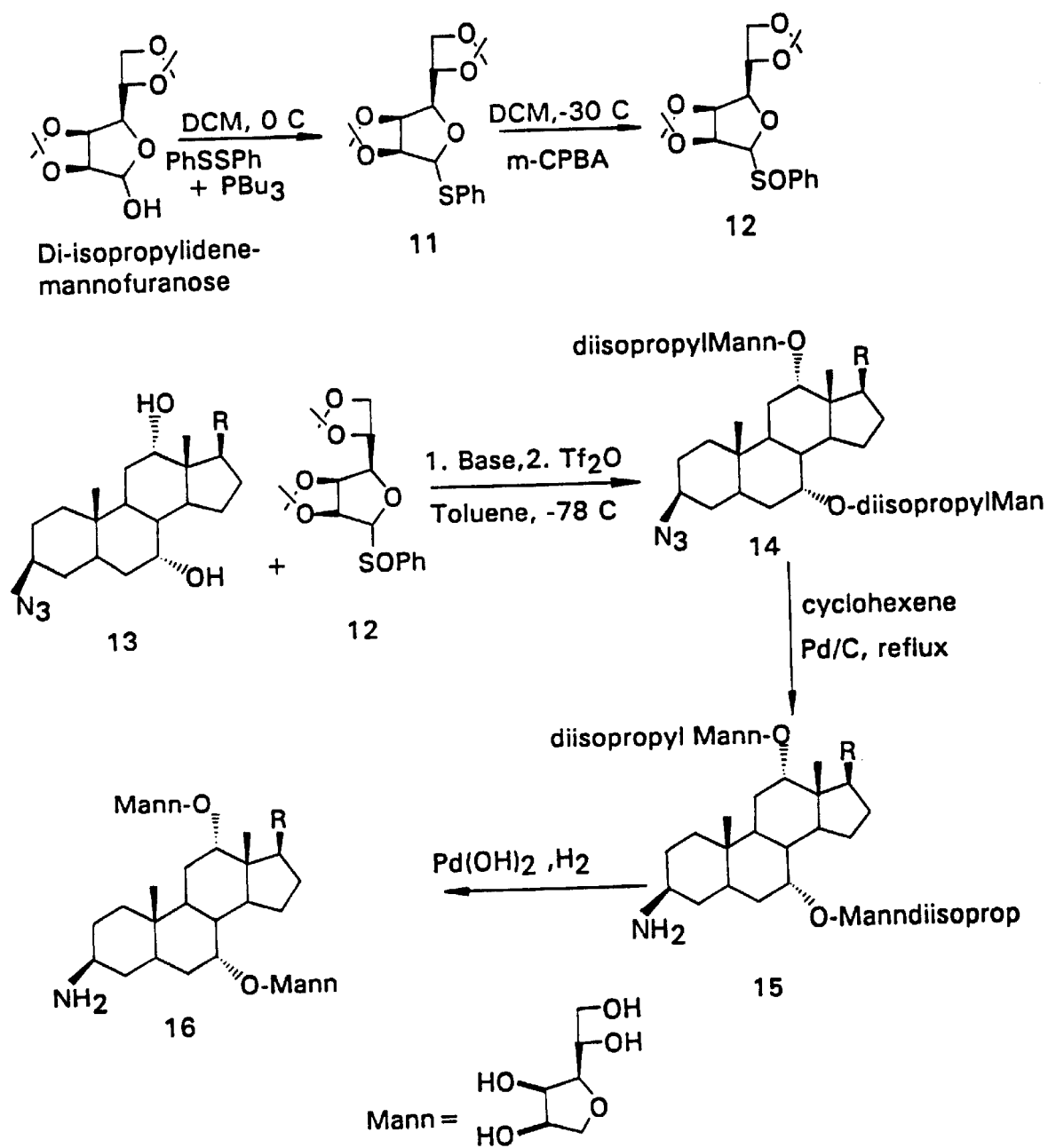
FIG. 7. Synthetic scheme for the preparation of methyl 3β-amino-7α,12α-bis(O-D-mannofuranosyl-1')cholate.

7. Synthesis of the Methyl 3β-Amino-7α,12α-bis (O-D-mannofuranosyl-1')cholate (16) (See, FIG. 7)

7.1. Phenyl 2:3,5:6-Diisopropylidene-1-thiomannofuranoside (11)

A mixture of diisopropylidene-mannose (25 g, 96 mmol), phenyldisulfide (25 g, 115 mmol), and tributylphosphine (24.2 g, 20 mL, 120 mmol) in DCM (200 mL) is stirred at 0° C. for 4 h. The solvent and excess of tributylphosphine are then evaporated. Petroleum ether is added and a seed crystal, if available, is added to the stirred solution. The crystals are filtered after 10 h. Weight 22.6 g (yield 80%); m.p. 110° C. (from hexane). $R_f$=0.65 (silica, EA/Hexane 2/5). IR (KBr) 3060, 3030, 1585, 1490, 1453, 1360, 1125, 1090, 1070 cm$^{-1}$. $^1$H NMR (CDCl$_3$), δ 7.7–7.0 (m, 5H), 3.95–5.1 (m, 7H), 1.25–150 (g, 12H).

7.2. Phenyl Sulfonyl 2:3,5:6-Diisopropylidene-mannofuranoside (12)

Mannosylsulfide 11 (22 g, 62 mmol) is dissolved in DCM (150 mL) and chilled to −78° C. Then, m-CPB (17 g, 70 mmol) in EA (100 mL) is added dropwise over 1 h. When TLC shows the spot of the product 12 only, a saturated solution of sodium bisulfite (9100 mL) is poured into the reaction mixture. The organic layer is washed with sodium bicarbonate, brine, dried and evaporated to give an oil, which is purified by flash chromatography (EA/Hexane, gradient from 0% to 50% of EA). Two fractions were collected. The first one $R_f$0.15 (EA/Hexane 2/5), weight 5.0 g, does not work in the coupling reaction and may be discarded. The second one ($R_f$–0.10, weight 15 g, 65% yield) works in the coupling reaction. Melting point 110° C. IR (KBr) 3060, 3030, 2900, 2870, 1490, 1370, 1230, 1130, 1090 cm$^{-1}$. $^1$H NMR (CDCL$_3$) δ 7.7–7.1 (m, 5H), 5.1–4.4 (m, 7H), 1.5–1.25 (m, 12H)

7.3. Methyl 3β-Azido-7α,12α-bis(O-2:3,5:6-diisopropylidene-D-mannofuranosyl-1')cholate (14)

The sulfoxide 12 (0.96 g, 2.5 mmol), the methyl 3β-azido-cholate 13 (2.5 mmol), and 2,6-diisopropyl-4-methyl-pyridine (0.63 g, 3.3 mmol) are dissolved in 100 mL of toluene and chilled to −78° C. under Ar. Triflic anhydride (0.56 mL, 3.3 mmol) is then added. After the addition, stirring is continued for 1 h at −78° C. The reaction mixture is then allowed to worm to −25° C. during 1 h. The reaction is quenched with a saturated solution of the sodium bicarbonate (50 mL) and the organic layer is washed with water, brine, dried over sodium sulfate and evaporated under reduced pressure. The residue is dissolved in hexane (25 mL), the insoluble part being filtered off. The clear filtrate is purified by flash chromatography (silica, EA/Hexane, gradient from 0% to 25% of EA). The pure substance 14 is isolated as a thick oil: weight 0.45 g (60% yield). $R_f$=0.65 (silica, EA/Hexane 2/5). IR (neat) 2108, 1734 cm$^{-1}$. $^1$]H NMR (CDCL$_3$) δ 5.18–3.95 (m, 14H), 3.68 (s, 3H), 1.4–1.2 (m, 24H), 0.96 (d, 3H), 0.88 (s, 3H), 0.59 (s, 3H).

7.4. Methyl 3β-Amino-7α,12α-bis(O-D-mannofuranosyl-1') cholate (16)

The purified azidoderivative 14 (0.4 g, 04 mmol) is dissolved in methanol/hexene (10 mL/15 mL) and 10% Pd/C (100 mg) is added. The reaction mixture is refluxed under Ar with stirring for 24 h. TLC (silica, EA/Hexane 2/5) shows the disappearance of the starting material and the appearance of a new spot on the base line. The catalyst is filtered off, and the filtrate is evaporated under reduced pressure to give the amino derivate 15 as a thick oil. $R_f$=0.8 (silica, DCM/EtOH 101), IR (neat) 3400 ($v_{NH}$), 1742 ($v_{COOMe}$). The isopropylidene protecting groups of 15 are hydrolyzed and isolated without further purification as shown in FIG. 18. The crude oil is dissolved in 80% acetic acid (10 mL) and heated under reflux for 6 h. The reaction mixture is diluted with water (20 mL), and a slight precipitate is filtered off. The clear filtrate is evaporated under reduced pressure to give a semi-solid residue of 16. This solid is rinsed with ethyl acetate (5 mL), filtered, dried in a desiccator, dissolved in water, and purified by reverse-phase column chromatography (CHP-20P column; 0–50% methanol-water). Any chromatography solvent is removed under reduced pressure. Freeze-drying affords the substance 16 as a white powder (0.155 g, 50% yield). $R_f$=0.8 (silica DCM/MeOH/iso-Propylamine 6/2/2); IR (neat)$_{8,430H,NH}$3400, $v_{COOMe}$1734 cm$^{-1}$; $^1$H NMR (CDCl$_3$) δ 5.13 (d, 2H), 4.1–3.2 (m. 14H), 3.53 (s, 3H), 1.0–1.2 (m, 25H), 0.817 (d, 3H), 0.744 (s, 3H), 0.465 (s, 3H). Anal. Calcd. for C$_{37}$H$_{63}$NO$_{14}$: C, 59.6; H, 8.44; N, 1.87%. Found: C, 58.8; H, 8.33; N, 2.37%. MS: M−OH+Na$^+$=750. Found 750.

Figure 8:
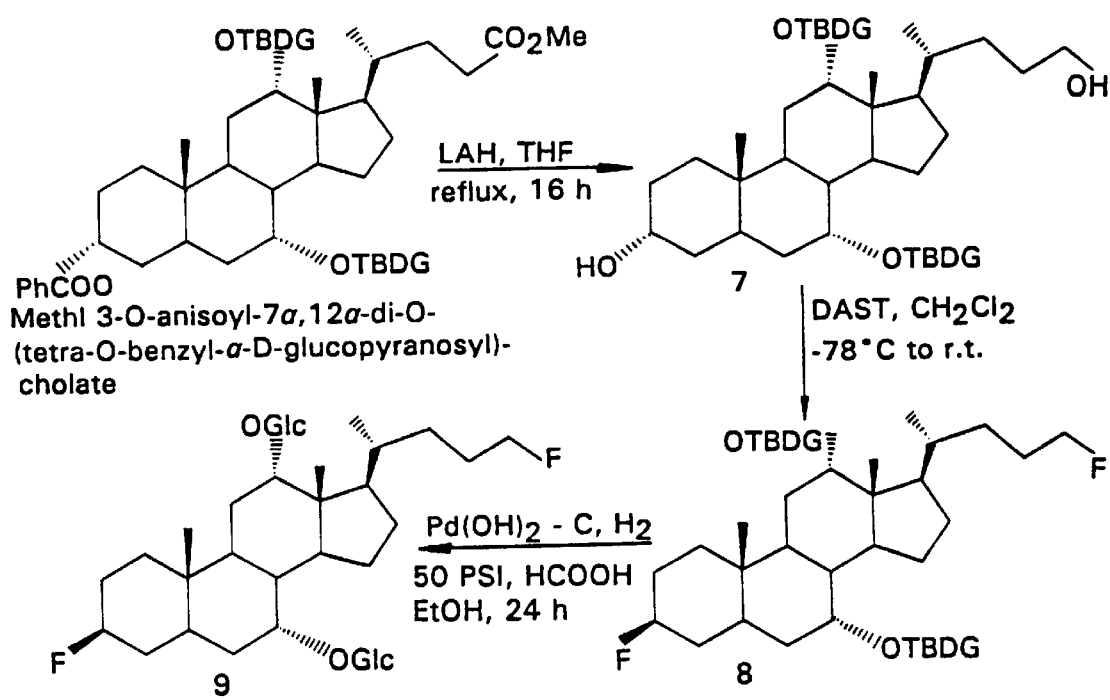
FIG. 8. Synthetic scheme for the preparation of 3β,24-difluoro-7α,12α-di(1'α-glucosyl)-5β-cholane.
Figure 9A:
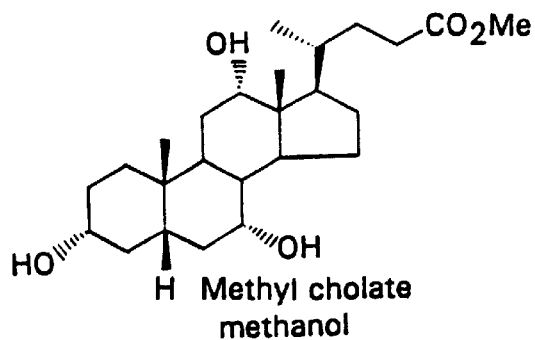
FIG. 9. Listing of solvent or solvent mixtures for recrystallization of selected reagents, intermediates or products.
Figure 9B:
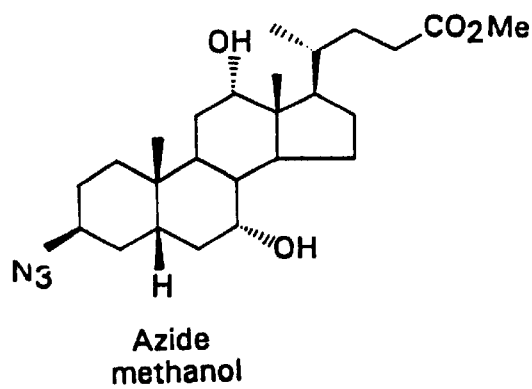
Figure 9C:
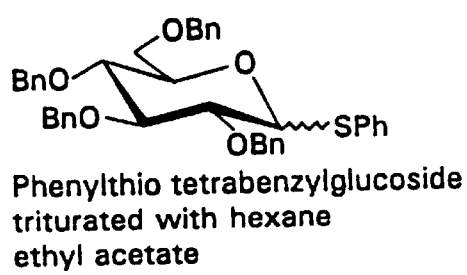
Figure 9D:
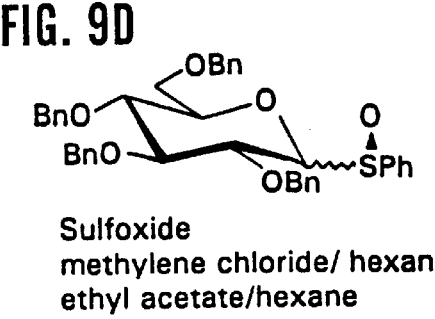
Figure 9E:
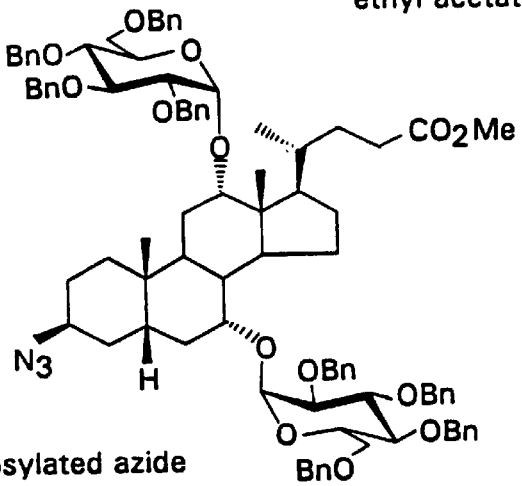

8. Synthesis of 3β,24-Difluoro-7α,12α-di(1'α-glucosyl)-5β-cholane (9) (See, FIG. 8)

8.1. 3α,24-Di-hydroxy-7α,12α-di(2',3',4',6'-tetra-O-benzyl-1'α-glucosyl)-5β-cholane (7)

To a mixture of lithium aluminum hydride (1.14 g, 30 mmol) in anhydrous tetrahydrofuran (100 mL), methyl 3O-anisoyl-7α-12α-di(2',3',4',6α-tetra-O-benzyl-1α-glucosyl)-5β-cholate (4.8 g, 3 mmol) in anhydrous tetrahydrofuran (100 mL) is added slowly at room temperature. Afterward, the contents of the reaction vessel are heated under reflux for 16 h. The mixture is then allowed to cool and excess lithium aluminum hydride is destroyed by the dropwise addition of aqueous sodium hydroxide (30 mL). The reaction mixture is acidified with 1N hydrochloric acid (40 mL) and extracted with methylene chloride (2×100 mL). The organic layer is washed with water (2×200 mL), dried (Na$_2$SO$_4$), and concentrated. The residue on flash chromatography (EtOAC:Hexane=1:2) gives 7 (2.6 g, 60%) as a white foam (mp 48°–50° C.). TLC $R_f$ (solvent—EtOAC:Hexane=1:2) 0.5. IR (KBr): 3445, 3086, 3057, 2930, 2868, 1491, 1457, 1364, 1153, 1073 cm$^{-1}$. $^1$H NMR (CDCl$_3$): δ 7.50–6.90 (m, 40H), 5.05–3.40 (m, 30H), 2.50–0.70 (m, 41H). Fab MS: 1462 (M+Na)$^+$. Anal. Calc. for C$_{92}$H$_{110}$O$_{14}$: C, 76.73; H, 7.71. Found: C, 76.04; H, 7.65.

8.2. 3β,24-Difluoro-7α,12α-di(2',3',4',6'-tetra-O-benzyl-1'α-glucosyl)-5β-cholane (8)

To a cooled (−78° C.) solution of compound 7 (1.45 g, 1 mmol) in anhydrous methylene chloride (50 mL), is added diethylaminosulfur trifluiride (0.35 mL, 2.65 mmol) with stirring for 15 min. The temperature is raised slowly to r.t. (over 30 min) and then saturated aqueous sodium bicarbonate (50 mL) is added. The reaction mixture is stirred for 15 min. The organic layer is separated, washed with water (2×50 mL), dried (Na$_2$SO$_4$), and concentrated. The residue, on flash chromatography (EtOAC:Hexane=3:17), gives 8 (700 mg, 49%) as an oil. TLC $R_f$ (solvent—EtOAC:Hexane=1:3) 0.7. IR (KBr): 3090, 3065, 3032, 2923, 2878, 1492, 1456, 1362, 1208, 1075 cm$^{-1}$. [$^1$]H NMR (CDCl$_3$): δ7.40–6.90 (m, 40H), 5.08 9d, 1H, J=3 Hz), 5.05 (d, 1H, J=3 Hz), 4.95–3.40 (m, 28H), 2.70–0.70 (m, 39H). Fab MS: 1465 (M+Na)$^+$. Anal. Calc for C$_{92}$H$_{108}$O$_{14}$F$_2$: C, 76.53; H, 7.54. Found: C, 76.40; H, 7.68.

8.3. 3β,24-Difluoro-7α,12α-di(1'α-glucosyl)-5β-cholane (9)

Compound 8 (577 mg, 0.4 mmol) is subjected to hydrogenolysis to give (173 mg, 60%) as a white form (mp 180°–182° C.). TLC $R_f$ (solvent—MeOH:CH$_2$D1$_2$:Isopropylamine—2:2:1) 0.7. IR(IBr): 3087, 3063, 3030, 2921, 2865, 1454, 1160, 1070 cm$^{-1}$. $^1$H NMR (DMSO-d$_6$ and two drops of $_2$D O): 54.85 (d, 1H, J=4.2 Hz), 4.67 (d, 1H, J=#0.6 Hz), 4.43 (t, 1H, J=5.6 Hz), 4.27 (t, 1H, J=5.6 Hz), 3.89 (s, 1H), 3.60–3.00 (m, 7H), 2.47–0.6 (m, 37H). Fab MS: 746 (M+Na)$^+$. Anal. Calc. for C$_{36}$H$_{60}$O$_{12}$F$_2$.2H$_2$O: C, 56.96; H, 8.50. Found: C, 57.04; H, 8.47.

9. Synthesis of 3-Azido Methylcholate in DMSO

Sodium azide (0.17 kg, 1.5 equivalents) is added at room temperature to a solution of 3-tosyl methylcholate (1.0 kg) in 2.5 kg of dimethylsulfoxide. This mixture is stirred and heated to 90° C. for 2 hr. The reaction is cooled to 65°–70° C. followed by the addition of methanol (2.5 kg), followed by the addition of water (1.5 kg). This mixture is cooled to 0° C. The resulting crystalline solid is filtered and washed with a methanol-water mixture. The resulting white solid is recrystallized from methanol. The desired 3-azido methylcholate is obtained in 66% overall yield as a white crystalline solid (mpt=149°–150° C.).

$^1$H NMR (CDCl$_3$) δ 7.77(2,d), 7.29(2,d), 4.25(1,m), 3.88 (1,s), 3.8(1,s), 3.65(3,s), 2.43(3,s), 0.95(3,d), 0.84(3,s), 0.65 (3,s).

10. Optimized Glycosylation of Methyl 3-Tosyloxycholate. Subsequent Reaction with Sodium Azide The preparation of the bis(glycosylated)tosyl intermediate was prepared according to the scheme, illustrated below. The conditions for its subsequent conversion to the 3-azido compound is also shown.

ambient temperature. (A precipitate of the pyridine hydrochloride forms within one hour of the start of the reaction.)

The following day, TLC analysis (ethyl acetate:hexane, 3:7) indicates the presence of the desired product (Rf 0.3) only. Any trace of the starting material (Rf 0.1) can be removed by purification through a silica gel column. The use of a large excess of tosyl chloride (e.g., a two-fold molar excess) should be avoided as the formation of the undesired 7-tosyloxy isomer (Rf 0.4, mp 127° C.) becomes problematic. Other side products, which may comprise up to 20 percent of the product mixture, may also appear at these higher levels of tosyl chloride. One such yellow impurity was characterized as having a maximum UV absorbance at 440 nm. The impurity may be removed by adsorption onto activated charcoal. At the conditions described above, however, which utilizes a 20 percent molar excess of tosyl chloride, little if any impurities are present.

The reaction product is acidified with the dropwise addition of a chilled acid solution prepared by combining concentrated HCl (10 mL) and 100 mL of water. The mixture is cooled with an ice bath, as necessary, to prevent the temperature of the mixture from exceeding room temperature.

The resulting solution is diluted twice with water (200 mL). A precipitate may form during the addition. Ethyl

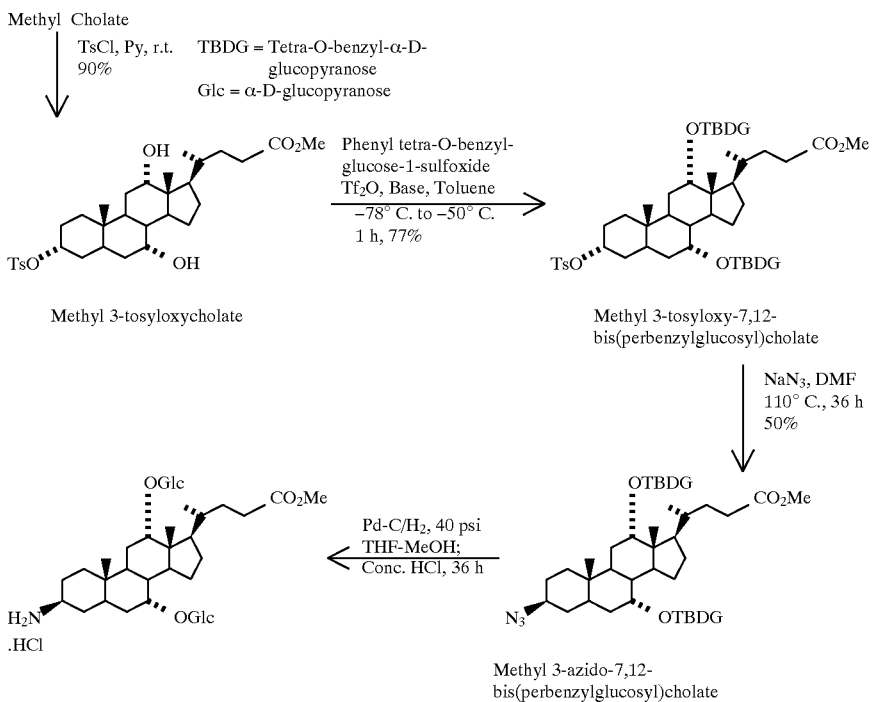

10.1. Synthesis of Methyl 3-Tosyloxycholate

Methyl cholate (15 g, 35.5 mmol) is dissolved in toluene (600 mL) and is dried by azeotropic distillation under vacuum in a rotary evaporator at 80° C. If necessary, the residual toluene can be removed using a Dean-Stark apparatus. The dried starting material is dissolved in pyridine (30 mL) at r.t.

Next, tosyl chloride (8.15 g. 42.7 mmol, 20% molar excess) is dissolved in 10 mL of pyridine and the resulting solution is added dropwise to the solution of methyl cholate with stirring over a 10 min period with external chilling if necessary to maintain the temperature in the range of about 10°–30° C. The reaction mixture is stirred overnight at acetate (100 mL) is added next; the resulting mixture is stirred and subsequently transferred to separatory funnel. The pH of the aqueous phase that separates is then tested and should ideally be in the range of about 3–5.5. If pH falls, instead, in the range of about 6.0–7.0, the mixture should again be washed with the diluted HCl solution prepared above (50 mL). Afterwards, the mixture is washed with deionized water (2×100 mL), brine (50 mL), and is poured into a flask containing 50 g of sodium sulfate. The mixture is then stirred for 2 h. Silica (5 g) is then added and the resulting mixture is stirred 1 h. Afterward, the contents of the flask are filtered through a column of silica (5 g) into a round bottom flask.

The solvent is evaporated under vacuum at 70° C. The residue is dissolved in methanol (60 mL). Activated carbon (3 g) is then added, and the resulting mixture is stirred for 10 min at 70° C. The mixture us then allowed to cool to r.t., filtered, and washed with methanol (10 mL).

In an Erlenmayer flask (1.0 L capacity) equipped with a stirrer bar is filled with 300 g of ice and 500 mL of dilute aqueous solution of HCl (conc. HCl to water, 1:100). The methanol solution from the previous step is then added dropwise to ice/HCl/water mixture with intense stirring. This procedure takes 1–2 h, and the white crystalline product should precipitate at the bottom to give a clear supernatant layer. The mixture is stirred overnight, filtered the following morning, and washed with water (2×50 mL) to neutral pH. The solid is pressed and dried in a dessicator over NaOH: 18.4 g (90% yield); mp 86°–88° C., purity 97% by HPLC.

The methyl 3-tosyloxycholate exists in an amorphous (mp 88° C.) and a crystalline form (mp 131° C.). The crystalline form is obtained by recrystallization from ether; that is, 3.0 g of the methyl 3-tosyloxycholate is dissolved in 6 mL of ether at r.t. After ca. 2 days the crystalline product begins to separate and is isolated by filtration. On melting, the crystalline form reverts to the amorphous form, which melts at the lower temperature.

10.2. Glycosylation Reaction in Methylene Chloride Solvent

The glycosylation of methyl 3-tosyloxycholate (3.456 g, 6 mmol) using the above-indicated sulfoxide (11.676 g, 18 mmol), triflic anhydride (3.2 mL, 19 mmol) and base (2.050 g, 10 mmol) in methylene chloride solvent (60 mL) is carried out as shown, above. After the recommended reaction period and usual workup, the product mixture is purified on a flash column, according to a method described elsewhere in the disclosure. TLC analysis shows that the isolated product migrates with an authentic sample. Proton NMR analysis of isolated product indicates the presence of a mixture of two compounds, the major component being the desired β isomer.

The glycosylated product is next subjected to nucleophilic displacement with sodium azide. After the reaction is allowed to proceed to completion, the product is worked up in the usual fashion. Proton NMR of the crude azido product indicates the absence of any α glycosylated azido compound. The majority of the product obtained is the desired β glycosylated azido compound, along with some other isomers. The results of this study gives a clear indication that the steroid glycosylation stereochemistry can be strongly influenced by the judicious choice of reaction solvent.

10.3. Semi-Large Scale Conditions for the Glycosylation Reaction

A semi-large scale reaction is carried out, as follows: The methyl 3-tosyloxy cholate (28.08 g, 50 mmol), sulfoxide (97.3 g, 150 mmol), triflic anhydride (26 mL, 155 mmol) and base (17.11 g, 83.3 mmol) are combined in toluence (600 mL), as described previously. The crude product (150 g) is washed with hot hexane (400 mL). The hexane is decanted, and the product is next washed with cold methanol (500 mL). These washings reduce the product weight to ca. 90 g. Some of the washed product (6.48 g) is subjected to the above-described sodium azide displacement reaction. It is observed that the reaction takes longer to complete (48 h versus 24 h at 120° C. for pure glycosylated product). As is usually observed, the desired isomer does not crystallize out. It is preferred, thus, that the glycosylated product be first purified before subjecting it to the sodium azide displacement reaction. Flash chromatographic purification of the semi-large scale crude product furnishes ca. 60 g (75%) of pure product mixture.

Therefore, the most preferred way to prepare the desired 3-azido compound appears to be through the glycosylation of methyl 3-tosyloxycholate. It is has been found that smaller amounts of the sodium azide are required via this route. For example, the displacement reaction involving 1.622 kg of bis(glycosylated)tosylcholate requires only 195 g of sodium azide in DMF solvent. The amount of sodium azide can be further reduced with the use of methyl pyrolidinone as solvent.

10.4. Reduction of the 3-Azido Compound, Followed by Debenzylation to Obtain Methyl 3β-amino-7α,12α-di(1'α-glucosyl)-5β-cholate·HCl Salt Methyl 3β-azido-7α,12α-di(2',3',4',6'-tetra-O-benzyl-1'α-glucosyl)-5β-cholate (44.79 g, 30 mmol) and conc. HCl (7.5 mL, 90 mmol) are combined in a solvent mixture comprised of tetrahydrofuran (200 mL) and methanol (200 mL). To this acidic mixture is added 10% palladium on activated carbon (45 g, wet and Degussa type, Aldrich Chemical, Co.). The resulting mixture is stirred for 36 h under an atmosphere of hydrogen (40 psi). Afterward, TLC analysis indicates complete hydrogenolysis. The product mixture is filtered through a layer of CELITE, sand, and a membrane filter. The filtrate is then concentrated. Recrystallization of the residue (22 g crude product) in 50 mL methanol gives 12.1 g of the desired product (51.6% yield, mp 198°–200° C. with decomp.). TLC $R_f$ 0.2 (solvent— MeOH:CH$_2$Cl$_2$:Isopropylamine=2:1:1). IR (KBr): 3395 (br), 2934, 1735, 1720, 1638, 1629, 1512, 1457, 1441, 1379, 1150, 1045, 1024 cm$^{-1}$. $^1$H NMR (CDCl$_3$): δ 5.06 (d, 1H, J=4.2 Hz), 4.80 (d, 1H, J=4.2 Hz), 3.95 (s, 1H), 3.80–3.20 (m, 14H), 2.60–1.00 (m, 28H), 0.89 (s, 3H), 0.79 (d, 3H J=5.7 Hz) and 0.64 (s, 3H). MS (Fab): 769 (M+Na)$^+$. Anal. Calc. for C$_{37}$H$_{64}$O$_{14}$N$_1$: C, 56.82; H, 8.25; N, 1.79; Cl, 4.48 Found: C, 52.21; H, 7.92; N, 1.62; Cl (Halogen estimate), 4.67.

11. Preparation of Phenyl 2,3,4,6-Tetra-O-Benzyl-1-Thio-β-D-Glucose (Precusor to the Corresponding Sulfoxide)

Starting from commercially available α,β-D-Glucose Pentaacetate (Pfanstiehl), the title compound is prepared in three steps with 53% overall yield and >96% HPLC purity.

11.1. Preparation of Phenyl-2,3,4,6-Tetraacetyl-1-Thio-β-D-Glucoside

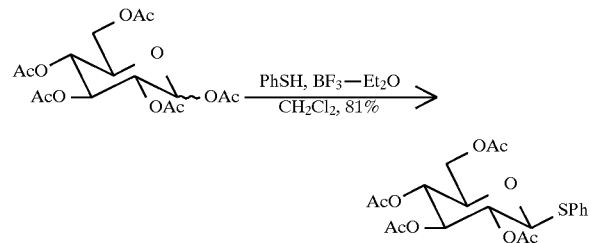

A 5 L three-necked round-bottom flask equipped with a heating mantle, mechanical stirrer (glass shaft/teflon paddle), condenser, addition funnel (125 mL) and nitrogen inlet is charged with 301.7 g (0.77 mole) of α,β-D-glucose pentaacetate dissolved in dichloromethane (1 L). Thiophenol (87.3 mL, 0.85 mole) is transferred to the addition funnel using a canula and vacuum hand pump. The thiophenol is added dropwise to the pentaacetate/dichloromethane solution with stirring at ambient temperature under nitrogen.

Upon completion of the addition, boron trifluoride etherate (47.5 mL, 0.38 mole) is added dropwise via a second addition funnel to the reaction mixture under nitrogen at room temperature. The reaction mixture is allowed to stir at ambient temperature for ½ hour and then is heated to reflux for 2 hours. The progress of the reaction is monitored by TLC in which the disappearance of starting materials and the appearance of a new product is noted.

The reaction mixture is cooled to ambient temperature at which point saturated aqueous sodium bicarbonate (500 mL) is added dropwise via an addition funnel. The reaction is quenched at a sufficiently slow rate such that no excessive amount of heat is generated and no uncontrolled evolution of gas occurs. It is observed that upon addition of the aqueous sodium bicarbonate, the reaction mixture changes color from a deep red to a clear slightly yellow. Stirring is continued until it is evident that all gas evolution has ceased.

The crude reaction mixture is transferred to a 2 L separatory funnel, and the lower organic layer is removed. The organic layer is washed once with distilled water (700 mL), followed by saturated aqueous solution of sodium chloride (700 mL). The organic layer is dried over sodium sulfate (500 g), filtered, and concentrated to yield 381.3 g of a plate yellow oil which solidifies upon standing. The crude product is further purified by trituration with 8/2 hexane/ethyl acetate (500 mL), with the aid of a mechanical stirrer. The white solids, which remain, are isolated by vacuum filtration. The product is washed further with hexane (2×500 mL) and allowed to air dry. Further drying can be accomplished by placing the compound in a vacuum desiccator at 5 mm Hg and 40° C. overnight. The final yield of the white solid is 277.0 g (81.4%).

TLC (silica gel): $R_f$ 0.35 in 30% ethyl acetate/hexane, UV visualized. HPLC: $R_T$ 3.1 min. (column, C-18 Phenomenex analytical, 25 cm×4.6 mm, 5μ; solvent, 100% acetonitrile; flow, 1 mL/min; detection, UV at 254). MS (positive ion FAB/DIHEDS/NaI): m/e 463 (M+Na), 331 (M-SC$_6$H$_5$). $^1$H-NMR (CDCl$_3$/TMS): 7.56–7.23 (5H, M, aromatic), 5.21 (1H, t, H-2), 5.01 (2H, dt, H-3 and H4), 4.72 (1H, d, anomeric H-1), 4.21 (2H, m, H-6 an H-6'), 3.71 (1H, m, H-5), 2.07 (3H, s, C=OC$\underline{H}_3$), 2.06 (3H, s, C=OCH$_3$), 2.00 (3H, s, C=OCH$_3$), 1.97 (3H, s, C=OCH$_3$). $^1$C-NMR (CDCl$_3$/TMS) 170.3 (C=O), 169.8 (C=O), 169.1 (C=O), 168.9 (C=O), 132.8 (aromatic), 131.4 (o-aromatic), 128.7 (m-aromatic), 128.2(p-aromatic), 85.4 (anomeric C-1), 75.5, 73.7, 69.7, 67.9, 61.8, 20.5 (CH$_3$), 20.3 (CH$_3$). Microanalysis, Calculated for C$_{30}$H$_{24}$O$_9$S: C, 54.54; H, 5.49; O, 32.69; S, 7.28, Found: C, 54.54; H, 5.45; S, 7.19.

11.2. Synthesis of Phenyl-1-Thio-β-D-glucoside

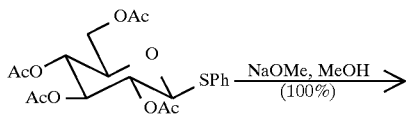

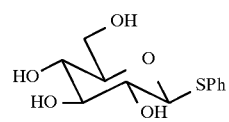

A 5 L three-neck round-bottom flask equipped with a mechanical stirrer, thermometer, and 500 mL addition funnel is set-up and flame dried under vacuum. The set up is then allowed to cool with a nitrogen sparge. The tetraacetyl intermediate (275.0 g, 0.62 mol) is loaded into the cooled round bottom. Anhydrous methanol (Aldrich SURE-SEAL, 1000 mL) is added via canula and a hand pump, and the white suspension is stirred with cooling (ice bath, 0°–5° C.).

Fresh sodium methoxide is prepared by weighing out hexane-washed sodium metal (0.96 g, 0.041 mol) and adding the weighed out metal to anhydrous methanol (200 mL) in separate flamed dried round bottom flask under a nitrogen atmosphere. Care should be taken to add the sodium metal to the methanol at a rate that is slow enough not to generate an exotherm.

The freshly prepared sodium methoxide is transferred to the addition funnel and is added dropwise to the cooled stirring reaction mixture. Again, the temperature is maintained in the reaction pot so as not to create an exothermic reaction.

Upon completion of the addition (ca. 20 minutes), the ice-bath is removed. The white heterogenous solution rapidly turns to a clear, colorless homogeneous solution as the reaction warms to ambient temperature. The reaction is allowed to stir at room temperature for approximately 4 hours. The progress of the reaction is monitored by TLC.

Upon complete spot-to-spot conversion of starting materials to product, the reaction is worked up as usual. Dowex 50×8 anion exchange resin (H$^+$ form, washed and reactived) is added to the stirred reaction mixture in small solid batches until the pH of a dampened pH test strip changes from about 12 to 7. (This change requires about 1.5 g of H$^+$ resin.) This heterogeneous suspension is allowed to stir for an additional ½ hour.

The anion exchange resin is then removed by filtration, washed with methanol, and the filtrates are combined and concentrated in vacuo to leave a white solid foam (163 g, 100%). No further purification is required.

MS (positive FAB/DIHEDS/NaI): m/e 295 (M+Na). $^1$H-NMR (DMSO-d$_6$/TMS): 7.46–7.16 (5H, m, aromatic), 5.28 (1H, d, O$\underline{H}$ exchange with D$_2$O), 5.09 (1H, d, O$\underline{H}$ exchange with D$_2$O), 4.97 (1H, d, O$\underline{H}$ exchange with D$_2$O), 4.56 (2H, d and t, O$\underline{H}$ exchange with D$_2$O, anomeric H-1), 3.70 (1H, dd), 3.41 (1H, m), 3.15 (4H, m) . $^{13}$C-NMR (DMSO-d$_6$): 135.3 (aromatic), 129.8 (aromatic), 129.1 (aromatic), 126.4 (aromatic), 87.3 (anomeric C-1), 81.2, 78.4, 72.6, 70.0, 61.3 (C-6). Microanalysis, Calculated for C$_{12}$H$_{16}$O$_5$S: C, 52.93; H, 5.92; O, 29.38; S, 11.77. Found: C, 52.71; H, 6.00; S, 11.62.

11.3. Synthesis of Phenyl 2,3,4,6-tetra-O-benzyl-1-thio-β-D-Glucose

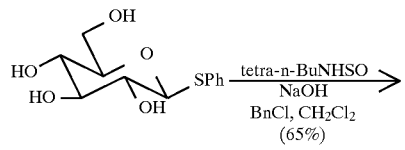

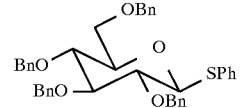

In a dried flask, phenylthioglucoside (149.0 g, 0.55 mol) is dissolved in 1.0 L of 10N NaOH with the aid of warming (40° C.). Upon dissolution, the clear vicous solution is transferred to a 5 L three-neck round-bottom flask, which is then fitted with a mechanical stirrer, thermometer, condenser, and nitrogen inlet. An additional 1.0 L of 10 N NaOH is used to rinse any remaining phenylthioglucoside from the first flask. The rinsings are then added to the 5 L reaction vessel.

Into a separate 2 L flask containing dichloromethane (500 mL) is placed tetrabutylammonium hydrogen sulfate (92.9 g, 0.27 mole). Benzyl chloride (319.5 g, 2.8 mol) in dichloromethane (500 mL) is added, and the mixture is stirred until fully dissolved. This solution is slowly added to the 5 L reaction flask under nitrogen. The resulting reaction mixture is stirred vigorously under nitrogen at room temperature overnight.

The progress of the reaction is monitored by TLC. Work-up includes allowing the reaction mixture to separate into two phases and removing the organic (upper) layer. The aqueous phase is washed with an additional 500 mL of dichloromethane. All organic layers are then combined. The organic phase is washed with 1M sulfuric acid (1000 mL), water (1000 mL), saturated aqueous sodium bicarbonate (1000 mL), and finally water (1000 mL).

The organic layers are dried over sodium sulfate, filtered, and concentrated to a pale yellow oil that solidifies upon standing. The final product is purified further by recrystallization from ethanol to give a white crystalline product in about 65% yield. mp (uncorrected) 89°–90° C. TLC (silica gel): $R_f$ 0.65 (80% hexane in ethyl acetate) UV visualized. HPLC $R_t$ 6.44 min, 95% purity (column, C-8 nucleosil; solvent, 90% MeOH in water, flow: 1.0 mL/min; detection, UV at 254). MS (FAB): m/e 655 (M+Na). $^1$H-NMR (CDCl$_3$/TMS): 7.61–7.19 (25H, m, aromatic), 4.91–4.50 (10H, m, benzylic C$\underline{H}_2$'s), 3.80–3.5 (7H, m, sugar C$\underline{H}_2$ and C$\underline{H}$). $^{13}$C-NMR (CDCl$_3$/TMS): 138.3, 138.2, 137.9, 133.7, 131.8, 128.4, 128.3, 128.2, 128.1, 127.8, 127.7, 127.6, 127.5, 127.4, 127.3, 87.3, 86.6, 80.7, 78.9, 77.7, 75.7, 75.3, 74.9, 73.3, 68.9. Microanalysis, Calculated for $C_{40}H_{40}O_5S$: C, 75.92; H, 6.37; O, 12.64; S, 5.07. Found: C, 75.67; H, 6.40; S, 4.96.

The corresponding sulfoxide reagent is then prepared from the sulfide by oxidation using meta-chloroperbenzoic acid in methylene chloride (83% yield), as described previously.

Other embodiments of the present invention will be evident to one of ordinary skill in view of the detailed descriptions provided herein. Such embodiments are considered to fall within the scope and spirit of the present invention, which invention is not limited to the preferred embodiments described above but only by the following claims.

What is claimed is:

1. A process for the production of 3-amino-substituted glycosylated bile acid derivatives comprising:
   (a) providing an ester of a bile acid having a hydroxyl substituent at the 3-position of the steroid nucleus, wherein the glycosyl group is protected;
   (b) converting said hydroxyl substituent at the 3-position into a leaving group;
   (c) subjecting said 3-substituted bile acid ester to reaction conditions which effect the glycosylation of any free hydroxyl group present in said steroid nucleus;
   (d) displacing said leaving group with an azido group with inversion of the stereochemistry at the 3-position to provide a 3-azido-substituted bile acid ester intermediate; and
   (e) reducing said azido substituent to provide a 3-amino-substituted glycosylated bile acid ester derivative.

2. The process of claim 1 in which glycosylation is carried out at a reaction temperature ranging from about −78° C. to about 20° C.

3. The process of claim 2 in which glycosylation is carried out at a reaction temperature of about −40° C.

4. The process of claim 1 in which displacement of the leaving group with an azido group is carried out in DMSO solvent.

5. The process of claim 4 in which displacement is carried out at elevated temperature.

6. The process of claim 5 in which displacement is carried out at about 90° C.

7. The process of claim 1 which further comprises removing protecting groups from the glycosyl moieties of said ester derivative.

8. The process of claim 7 which further comprises hydrolyzing said ester derivative to provide the free acid derivative.

9. The process of claim 1 which further comprises purifying said ester derivative by reverse-phase column chromatography.

10. The process of claim 1 which further comprises recrystallizing an intermediate or reaction product after a reaction step.

11. The process of claim 1 which further comprises recrystallizing a reagent before its use in a reaction step.

12. The process of claim 1 in which said leaving group is a tosylate, mesylate or triflate.

13. The process of claim 1 in which said reduction step is effected by ammonium formate and palladium on carbon.

14. The process of claim 1 in which said reduction step is effected by triphenyl phosphine.

15. The process of claim 1 in which said reduction step is effected by Raney nickel.

16. The process of claim 1 in which said glycosylation conditions employ a sulfoxide-based glycosylation procedure.

17. The process of claim 1 in which said bile acid is cholic acid, allocholic acid, deoxycholic acid or chenodeoxycholic acid.

18. The process of claim 1 in which said ester is a methyl ester.

19. A process for the production of 3-amino-substituted glycosylated bile acid derivatives comprising:
   (a) providing an ester of a bile acid having a hydroxyl substituent at the 3-position of the steroid nucleus, wherein the glycosyl group is protected;
   (b) converting said hydroxyl substituent at the 3-position into a leaving group;
   (c) displacing said leaving group with an azido group with inversion of the stereochemistry at the 3-position to provide a 3-azido-substituted bile acid ester intermediate;
   (d) subjecting said 3-azido-substituted bile acid ester intermediate to reaction conditions which effect the glycosylation of any free hydroxyl group present in said steroid nucleus; and
   (e) reducing said azido substituent to provide a 3-amino-substituted glycosylated bile acid ester derivative in which reduction of said azido substituent is carried out in a single step with removal of the protecting groups from the glycosyl moieties.

20. The process of claim 19 in which reduction and deprotection is effected by hydrogenolysis in an acidic protic solvent mixture over a metal catalyst.

21. The process of claim 20 in which said metal catalyst comprises palladium.

22. The process of claim 19 in which the order in which steps (c) and (d) are carried out is reversed.

23. The process of claim 19 in which glycosylation is carried out at a reaction temperature ranging from about −78° C. to about 20° C.

24. The process of claim 19 in which displacement of the leaving group with an azido group is carried out in DMSO solvent.

25. The process of claim 24 in which displacement is carried out at elevated temperature.

26. The process of claim 25 in which displacement is carried out at about 90° C.

* * * * *